US010513494B2

(12) United States Patent
Bertaccini et al.

(10) Patent No.: US 10,513,494 B2
(45) Date of Patent: Dec. 24, 2019

(54) METHODS, COMPOUNDS, AND COMPOSITIONS FOR ANESTHESIA

(71) Applicants: THE BOARD OF TRUSTEES OF THE LELAND STANFORD JUNIOR UNIVERSITY, Palo Alto, CA (US); THE UNITED STATES GOVERNMENT AS REPRESENTED BY THE DEPARTMENT OF VETERANS AFFAIRS, Washington, DC (US)

(72) Inventors: Edward John Bertaccini, San Jose, CA (US); Margaret Frances Davies, Palo Alto, CA (US)

(73) Assignees: The Board of Trustees of the Leland Stanford Junior University, Palo Alto, CA (US); The United States Government as represented by the Department Of Veterans Affairs, Washington, DC (US)

( * ) Notice: Subject to any disclaimer, the term of this patent is extended or adjusted under 35 U.S.C. 154(b) by 0 days.

(21) Appl. No.: 16/210,631

(22) Filed: Dec. 5, 2018

(65) Prior Publication Data
US 2019/0106387 A1   Apr. 11, 2019

Related U.S. Application Data

(63) Continuation of application No. 15/519,543, filed as application No. PCT/US2015/056067 on Oct. 16, 2015, now abandoned.

(60) Provisional application No. 62/064,670, filed on Oct. 16, 2014.

(51) Int. Cl.
*C07D 207/34* (2006.01)
*A61K 31/40* (2006.01)
*A61K 31/402* (2006.01)

(52) U.S. Cl.
CPC ............ *C07D 207/34* (2013.01); *A61K 31/40* (2013.01); *A61K 31/402* (2013.01)

(58) Field of Classification Search
CPC .................................................. C07D 207/34
See application file for complete search history.

(56) References Cited

U.S. PATENT DOCUMENTS

| | | | |
|---|---|---|---|
| 2,479,971 A | 8/1949 | Scholz | |
| 2,986,564 A | 5/1961 | Rips et al. | |
| 4,056,635 A | 11/1977 | Glen et al. | |
| 4,289,783 A | 9/1981 | Mesens | |
| 4,798,846 A | 1/1989 | Glen et al. | |
| 5,731,355 A | 3/1998 | Jones et al. | |
| 5,858,410 A | 1/1999 | Muller et al. | |
| 6,372,777 B1 * | 4/2002 | Martins | C07D 207/34 514/423 |
| 7,915,317 B2 | 3/2011 | Zhang et al. | |
| 8,383,687 B2 | 2/2013 | Harris et al. | |
| 8,557,856 B2 | 10/2013 | Raines et al. | |
| 8,765,973 B2 | 7/2014 | Raines et al. | |
| 8,796,340 B2 | 8/2014 | Theisinger et al. | |
| 2003/0013754 A1 | 1/2003 | Martins et al. | |
| 2006/0122230 A1 | 6/2006 | Berggren et al. | |

FOREIGN PATENT DOCUMENTS

| | | |
|---|---|---|
| WO | 01/47880 A1 | 7/2001 |
| WO | 2005/080328 A1 | 9/2005 |
| WO | 2006/087476 A2 | 8/2006 |
| WO | 2008/002974 A1 | 1/2008 |
| WO | 2009/141532 A2 | 11/2009 |
| WO | 2009/153569 A2 | 12/2009 |
| WO | 2011/023677 A1 | 3/2011 |

OTHER PUBLICATIONS

Jurd et al. (2003) Faseb J 17:250-2.
Bertaccini et al. (2002) Protein Eng 15:443-54.
Miyazawa et al. Nature 424:949-55.
Bertaccini et al. (2010) J Chem Int Model 50:2248-55.
Miller et al. (2014) Nature 512:270-5.
Murail et al. (2011) Biophys J 100:1642-50.
Bertaccini et al. (2010) ACS Chem. Neurosci. 1:552-558.
Szarecka et al. (2007) Proteins 68:948-60.
Mascia et al. (2005) Eur. J. Pharmacol. 516:204-211.
Bertaccini (2010) Pharmaceuticals 3:2178-2196.
Brooks et al. (2009) J Comput Chem 30:1545-614.
Roberts et al. (2006) J Biol Chem 281:3305-11.
Forman et al. (2012) Curr Opin Anaesthesiol 25:411-8.
Forman et al. (2011) Can J Anaesth 58:191-205.
Ruesch et al. (2012) Anesthesiology 116:47-55.
Stewart et al. (2013) Mol Pharmacol 83:1200-08.
Nu et al. (2003) J Comput Chem 24:1549-62.
Vedula et al. (2009) J Biol Chem 284:24176-84.
Krasowski et al. (2001) J Pharmacol Exp Ther 297:338-51.
Mihic et al. (1994) Mol Pharmacol 46:851-7.
Asproni et al. (2005) J Med Chem 48:2638-45.
Shanmugasundararaj et al. (2013) Anesth Analg 116:1249-56.
Koska et al. (2008) J Chem Inf Model 48:1965-73.
Bertaccini et al. (2013) Anesthesiology 119:1087-95.

(Continued)

*Primary Examiner* — Shawquia Jackson
(74) *Attorney, Agent, or Firm* — David A. Roise; VLP Law Group LLP

(57) ABSTRACT

Methods of treatment useful in the inducement or maintenance of anesthesia in a subject are provided. The methods comprise administering to a subject in need of anesthesia a compound disclosed herein. Also provided are novel compounds having anesthetic effects, pharmaceutical compositions comprising the compounds, and packaged pharmaceuticals. Computer modeling of the compounds demonstrates favorable interactions with the GABA receptor type A. In addition, the compounds display reversible anesthetic effects in an animal model, with dose-response curves similar to those of known general anesthetics. GABA receptor-mediated effects are also demonstrated in a hippocampal brain slice preparation.

20 Claims, 5 Drawing Sheets

(56) References Cited

OTHER PUBLICATIONS

PubChem-CID-24894335 Create Date: Sep. 22, 2008.
PubChem-CID-16111410 Create Date: Jun. 18, 2007.
Pejo et al. (2012) Crit Care Med 40:187-192.
Anesthesia—Wikipedia—Sep. 2014.
Li et al. (2013) RSC Adv. 3:22872-76 supporting information (DOI:10.1039/c3ra44595j).
Ke et al. (2013) Chem. Commun. 49:7549-51 supporting information (DOI:10.1039/c3cc43682a).
Demirayak et al. (2006) J. Enzyme Inhib. Med. Chem. 21:113-18 (DOI:10.1080/14756360500472845).
En et al. (2014) J. Org. Chem. 79:4456-62 (DOI:10.1021/jo500418s).
Morelli et al. (1960) J. Med. Pharm. Chem. 2, 79-90.
Butini et al. (2012) J. Med. Chem. 55, 6898-6915.

\* cited by examiner (A)  (B)

METHODS, COMPOUNDS, AND COMPOSITIONS FOR ANESTHESIA

CROSS-REFERENCE TO RELATED APPLICATION

This application is a continuation of U.S. patent application Ser. No. 15/519,543, filed on Apr. 15, 2017, which is a national phase application of PCT International Application No. PCT/US2015/056067, filed on Oct. 16, 2015, which claims the benefit of U.S. Provisional Application No. 62/064,670, filed on Oct. 16, 2014, the disclosures each of which are incorporated herein by reference in their entireties.

BACKGROUND OF THE INVENTION

For over 160 years, anesthetics have been given safely and effectively to minimize the otherwise deleterious side effects of major invasive procedures. Despite such success, their exact mechanism remains elusive. This is confounded by the fact that our understanding of the conscious state which general anesthesia alters is grossly inadequate. However, over the past years, great insights have been gained into the molecular underpinnings of anesthetic mechanisms, just as they have with comparable factors within the central nervous system. It is now believed that anesthetics mediate a significant portion of their activity via binding to and modulation of transmembrane ligand-gated ion channels (LGICs). In particular, the gamma-aminobutyric acid receptor type A (GABAaR) and the glycine alpha one receptor (GlyRa1) are ion channels whose inhibitory currents are potentiated by the presence of general anesthetics. It is the GABAaR whose perturbation by barbiturates and benzodiazepines produces a state strongly similar to general anesthesia. Likewise, the intravenous general anesthetics, propofol and etomidate, are thought to modulate consciousness through specific sites within these channels. Jurd et al. (2003) *Faseb J* 17:250-2. These ion channels are composed of five subunits, often heteropentameric and variable in stoichiometry, arranged around a central ion conducting pore. The extracellular domain of a representative subunit is characterized by a large component of beta sheet secondary structure and contains the binding site for the native ligand germane to the channel in question (i.e. gamma-aminobutyric acid (GAB A) for the GABAaR). The transmembrane domain is composed largely of four-helix bundles. This latter secondary structure is a significant feature predicted in the inventors' laboratory and later validated by experimentalists. Bertaccini et al. (2002) *Protein Eng* 15:443-54; Miyazawa et al. *Nature* 424:949-55. It is within this transmembrane region that anesthetics and alcohols are thought to bind and convey the majority of their channel modulation. Bertaccini et al. (2010) *J Chem Inf Model* 50:2248-55.

The LGICs are transmembrane proteins, and their isolation and purification has thus proven difficult. While a recently published crystal structure shows the homomeric GABAaR beta 3 in the desensitized state (Miller et al. (2014) *Nature* 512:270-5) (a state that is insensitive to most anesthetics and alcohols), high resolution crystal structures of the heteromeric GABAaR in the open state (a state that anesthetics are thought to stabilize) do not exist. However, molecular modeling approaches are beginning to provide significant progress towards an understanding of LGIC structure and the interactions of these proteins with anesthetics.

The mainstay of such calculations lies in the techniques of homology modeling. Homology modeling is the method by which the amino acid sequence of a protein of unknown structure is aligned and threaded over that of a closely related amino acid sequence with known three-dimensional structure, such that the coordinates of the known protein can be transferred to those of the unknown. While such homology modeling involves a great deal of computational theory, it is also very dependent on experimentally described coordinates of proteins to act as templates with high sequence homology to the desired protein. Bertaccini et al. (2010) *J Chem Inf Model* 50:2248-55; Murail et al. (2011) *Biophys J* 100:1642-50. Over the last several years, several templates with great homology to the LGICs have been determined via cryo-electron microscopy, X-ray crystallography, and nuclear magnetic resonance (NMR) that have made model construction more robust.

The inventors' new models, based on such a template, can account for much of the currently available experimental data concerning these channels, allowing correlation of ligand binding measures with experimental potencies. These models have been used to illustrate the mechanism of channel gating (Bertaccini et al. (2010) *ACS Chem. Neurosci.* 1:552-558; Szarecka et al. (2007) *Proteins* 68:948-60) and can be used as the bases for in silico high throughput screening and new anesthetic discovery, and, in particular, to identify lead compounds for further screening in animals.

An April 2010 statement by MarketResearch.com reported that the world anesthetic drug market is estimated to be $4.1 billion. The drug profiles and dangerous side effects of the currently available agents are many, however, especially amongst the aging population of geriatric patients. Proportionately, the fastest growing segment of the population are octagenerians and older, a group of people who are now responsible for the majority of healthcare expenditures and are in need of increasing surgical and anesthetic care. Therefore, there is significant clinical pressure as well as market opportunity to develop new anesthetic agents.

There are currently four main intravenous and three primary inhalational anesthetic agents which are in common clinical use. Each of these agents is associated with an entire spectrum of undesirable hemodynamic perturbations, most of which result in lower systemic blood pressure. This is a side effect that is poorly tolerated in the very young patient, with newly developing cardiovascular compensatory mechanisms, as well as in the elderly, with confounding comorbidities and otherwise exhausted compensatory mechanisms.

Each of the commonly-used anesthetic agents has additional unique detriments. In particular, etomidate is the agent which comes closest to achieving ideal cardiovascular preservations while inducing dose-dependent alterations in consciousness, but this is at the expense of clinically significant adrenal suppression via inhibited steroid biosynthesis. U.S. Pat. No. 8,557,856 describes etomidate analogues having alleged improved pharmacokinetic and pharmacodynamics properties. U.S. Pat. No. 8,765,973 describes etomidate analogues that allegedly do not inhibit steroid biosynthesis. None of these etomidate analogues has yet achieved clinical approval, however.

Propofol has gained wide popularity, but in the past few years has been the subject of a nationwide shortage and can produce profound hypotension. While no profit estimates can be given for new anesthetic agents at this time, the cost savings from greater titratability and minimal cardiopulmonary side effects, both of which should lead to shorter and less complicated hospital stays, would be substantial.

There is thus a need for improved anesthetic agents, particularly for use in very young patients, elderly patients, and in patients that are critically ill. There is likewise a need for pharmaceutical compositions containing the improved agents and for methods of treatment that involve administration of the agents to induce or maintain anesthesia.

SUMMARY OF THE INVENTION

The present invention addresses these and other problems by providing compounds, pharmaceutical compositions, kits, and methods of use of compounds that act as anesthetics.

In particular, according to one aspect of the invention, methods of treatment are provided that comprise administering to a subject in need thereof a concentration of a compound sufficient to induce or maintain anesthesia in the subject, wherein the compound is represented by structural formula (I):

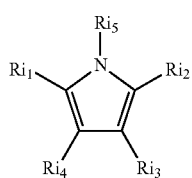

(I)

or a pharmaceutically acceptable salt thereof, wherein:

$R_{i1}$ and $R_{i2}$ are independently H, a lower alkyl group, or a phenyl group, wherein the alkyl group and phenyl group are optionally and independently substituted with one or more alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido groups, and wherein two adjacent substituent groups can combine to form a ring;

either $R_{i3}$ or $R_{i4}$ is —C(O)OR$_e$, and the other group is H or a lower alkyl group;

$R_e$ is alkyl, alkenyl, alkynyl, aryl, aralkyl, heteroaryl, heteroaralkyl, cycloalkyl, cycloalkenyl, heterocyclyl, or heterocyclylalky, and is optionally substituted with alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido; and $R_{i5}$ is a phenyl group optionally substituted with one or more alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido groups, and wherein two adjacent substituent groups can combine to form a ring.

Also provided are methods of treatment, wherein the compound is represented by structural formula (II):

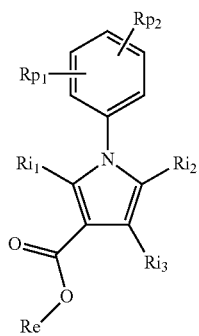

(II)

or a pharmaceutically acceptable salt thereof, wherein:

$R_{p1}$ and $R_{p2}$ are independently H, alkyl, alkenyl, alkynyl, alkoxy, alkanoyl, alkylamino, alkylthio, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido;

$R_{i3}$ is H or a lower alkyl group; and $R_{i1}$, $R_{i2}$, and $R_e$ are as defined above for structural formula (I).

In some of the methods, the compound is represented by structural formula (III):

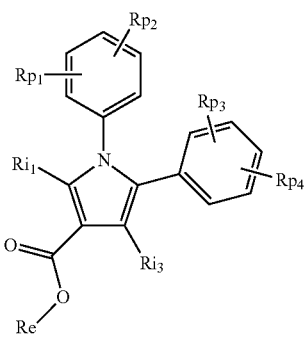

(III)

or a pharmaceutically acceptable salt thereof, wherein:
$R_{p1}$, $R_{p2}$, $R_{p3}$, and $R_{p4}$ are independently H, alkyl, alkenyl, alkynyl, alkoxy, alkanoyl, alkylamino, alkylthio, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido;

$R_{i3}$ is H or a lower alkyl group; and $R_{i1}$ and $R_e$ are as defined above for structural formula (I).

In another aspect, compounds are provided as represented by structural formula (II):

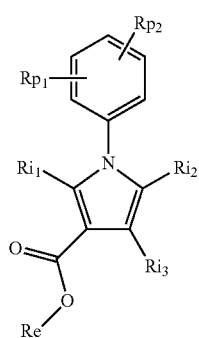

(II)

or a pharmaceutically acceptable salt thereof, wherein:
$R_{p1}$ and $R_{p2}$ are independently H, alkyl, alkenyl, alkynyl, alkoxy, alkanoyl, alkylamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, alkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, or azido, each of which may be optionally substituted where chemically feasible;

$R_{i1}$ is H or a $C_1$-$C_6$ alkyl group;

$R_{i2}$ is a phenyl group optionally substituted with one or more alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido groups, and wherein two adjacent substituent groups can combine to form a ring;

$R_{i3}$ is H or an unsubstituted lower alkyl group; and $R_e$ is $C_3$-$C_8$-alkyl, alkenyl, alkynyl, aryl, aralkyl, heteroaryl, heteroaralkyl, cycloalkyl, cycloalkenyl, heterocyclyl, or heterocyclylalky, and is optionally substituted with alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, or azido;

provided that when $R_{i1}$ is methyl, $R_{i2}$ is unsubstituted phenyl, and $R_e$ is benzyl, isopropyl, isobutyl, t-butyl, methoxyethyl, or 4,4-difluoro-3-methyl-3-buten-1-yl, and $R_{p1}$ is H, then $R_{p2}$ is not H;

when $R_{i1}$ is methyl, $R_{i2}$ is 2-methoxyphenyl, $R_e$ is t-butyl, and $R_{p1}$ is H, then $R_{p2}$ is not H, 3-amino, 3-azido, 4-bromo, or 4-nitro; and when $R_{i1}$ is methyl, $R_{i2}$ is 2-methoxyphenyl, $R_e$ is benzyl, and $R_{p1}$ is H, then $R_{p2}$ is not H.

In another aspect, compounds are provided as represented by structural formula (II):

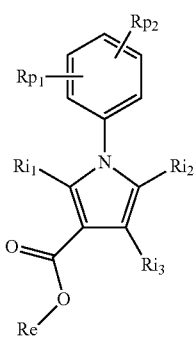

(II)

or a pharmaceutically acceptable salt thereof, wherein:
$R_{p1}$ and $R_{p2}$ are independently H, alkyl, alkenyl, alkynyl, alkoxy, alkanoyl, alkylamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, alkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, or azido, each of which may be optionally substituted where chemically feasible;

$R_{i1}$ is H or a $C_1$-$C_6$ alkyl group;

$R_{i2}$ is a phenyl group substituted with one or more alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido groups, and wherein two adjacent substituent groups can combine to form a ring;

$R_{i3}$ is H or an unsubstituted lower alkyl group; and $R_e$ is alkyl, alkenyl, alkynyl, aryl, aralkyl, heteroaryl, heteroaralkyl, cycloalkyl, cycloalkenyl, heterocyclyl, or heterocyclylalky, and is optionally substituted with alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, or azido;

provided that $R_{i2}$ is not 2-aminophenyl, 3-aminophenyl, 3-amino-4-hydroxyphenyl, 4-aminophenyl, 3-azidophenyl, 1,1'-biphenyl, 2-bromophenyl, 3-bromophenyl, 4-bromophenyl, 2-carboxyphenyl, 2-(chlorocarbonyl)phenyl, 4-chlorophenyl, 2,4-dichlorophenyl, 2,4-dimethoxyphenyl, 3,4-dimethoxyphenyl, 3,4-dimethylphenyl, 4-fluorophenyl, 2-methoxyphenyl, 3-methoxyphenyl, 4-methoxyphenyl, 3-(ethoxycarbonyl)phenyl, 4-(methoxycarbonyl)phenyl, 2-methylphenyl, 4-methylphenyl, 4-(methylsulfonyl)phenyl, 4-(methylthio)phenyl, 3-(4-morpholinylsulfonyl)phenyl, 2-nitrophenyl, 3-nitrophenyl, 4-nitrophenyl, 3-(phenylamino)phenyl, 4-(1H-pyrrol-1-yl)phenyl, 4-(1-methyl-1H-pyrazol-4-yl)phenyl, 2-hydroxy-5-aminophenyl, or 4-[5-(4-chlorophenyl)-3-(ethoxycarbonyl)-2-methyl-1H-pyrrol-1-yl]phenyl].

In still another aspect, compounds are provided as represented by structural formula (IV):

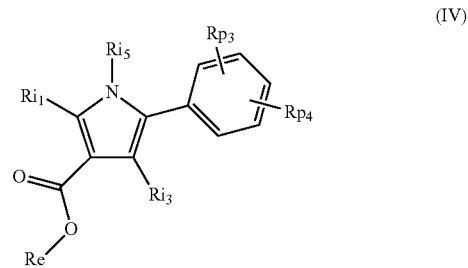

(IV)

or a pharmaceutically acceptable salt thereof, wherein:

$R_{p3}$ and $R_{p4}$ are independently H, alkyl, alkenyl, alkynyl, alkoxy, alkanoyl, alkylamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, alkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, or azido, each of which may be optionally substituted where chemically feasible;

$R_{i1}$ is H or a $C_1$-$C_6$ alkyl group;

$R_{i5}$ is a phenyl group substituted with one or more alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido groups;

$R_{i3}$ is H or an unsubstituted lower alkyl group; and $R_e$ is alkyl, alkenyl, alkynyl, aryl, aralkyl, heteroaryl, heteroaralkyl, cycloalkyl, cycloalkenyl, heterocyclyl, or heterocyclylalky, and is optionally substituted with alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, or azido;

provided that $R_{i5}$ is not 2-aminophenyl, 2-bromophenyl, 2-carboxyphenyl, 2-chlorophenyl, 2-(dimethylamino)phenyl, 2-ethylphenyl, 2-hydroxyphenyl, 2-methoxyphenyl, 2-methylphenyl, 2-nitrophenyl, 2-trifluoromethylphenyl, 3-acetylphenyl, 3-aminophenyl, 3-aminocarbonylphenyl, 3-azidophenyl, 3-bromophenyl, 3-butoxyphenyl, 3-carboxyphenyl, 3-chlorophenyl, 3-(dimethylamino)phenyl, 3-fluorophenyl, 3-hydroxylphenyl, 3-iodophenyl, 3-methoxyphenyl, 3-methylphenyl, 3-methylthiophenyl, 3-nitrophenyl, 3-trifluoromethylphenyl, 4-aminophenyl, 4-azidophenyl, 4-bromophenyl, 4-carboxyphenyl, 4-chlorophenyl, 4-ethoxyphenyl, 4-ethylphenyl, 4-fluorophenyl, 4-hydroxyphenyl, 4-methoxyphenyl, 4-methylphenyl, 4-nitrophenyl, 4-trifluoromethoxyphenyl, 4-(3,3,3-trifluoropropoxy)phenyl, 2,4-difluorophenyl, 2,4-dichlorophenyl, 3-amino-4-hydroxyphenyl, 3-carboxy-4-hydroxyphenyl, 2-hydroxy-5-aminophenyl, 2-bromo-4-acetylphenyl, 2,4-dibromophenyl, 2-bromo-4-(ethoxycarbonyl)phenyl, 2-bromo-4-fluorophenyl, 2-bromo-4-trifluoromethylphenyl, 3-hydroxy-4-carboxyphenyl, 3-carboxy-4-hydroxyphenyl, 2,6-diisopropylphenyl, 2,5-dimethoxyphenyl, 3,4-dimethoxyphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methoxy-4-methylphenyl, 2-methyl-3-chlorophenyl, 2,4-dichlorophenyl, 3,4-dichlorophenyl, 3,5-dichlorophenyl, 2-methoxy-5-nitrophenyl, 2-nitro-4-methylphenyl, or 2-chloro-5-trifluoromethylphenyl.

In yet another aspect, compounds are provided as represented by structural formula (II):

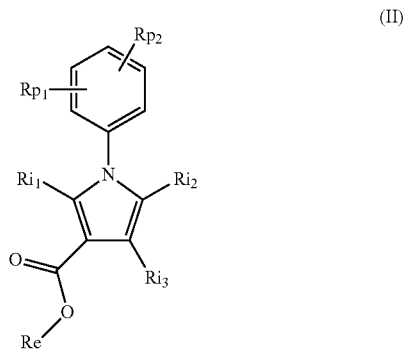

(II)

or a pharmaceutically acceptable salt thereof, wherein:

$R_{p1}$ and $R_{p2}$ are independently H, alkyl, alkenyl, alkynyl, alkoxy, alkanoyl, alkylamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, alkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, or azido, each of which may be optionally substituted where chemically feasible;

$R_{i1}$ is H;

$R_{i2}$ is a phenyl group optionally substituted with alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido, and wherein two adjacent substituent groups can combine to form a ring;

$R_{i3}$ is H or an unsubstituted lower alkyl group; and $R_e$ is alkyl, alkenyl, alkynyl, aryl, aralkyl, heteroaryl, heteroaralkyl, cycloalkyl, cycloalkenyl, heterocyclyl, or heterocyclylalky, and is optionally substituted with alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, or azido;

provided that when $R_{i2}$ is 4-(methylsulfonyl)phenyl, $R_e$ is methyl, and $R_{p1}$ is H, then $R_{p2}$ is not 4-fluoro; and when $R_{i2}$ is unsubstituted phenyl, $R_e$ is methyl, and $R_{p1}$ is H, then $R_{p2}$ is not 4-methoxy.

According to another aspect of the invention are provided pharmaceutical compositions comprising any of the compounds of the invention and a pharmaceutically acceptable carrier, as well as packaged pharmaceuticals comprising these pharmaceutical compositions and instructions for using the compositions to treat a mammalian subject.

DETAILED DESCRIPTION OF THE INVENTION

Figure 1:
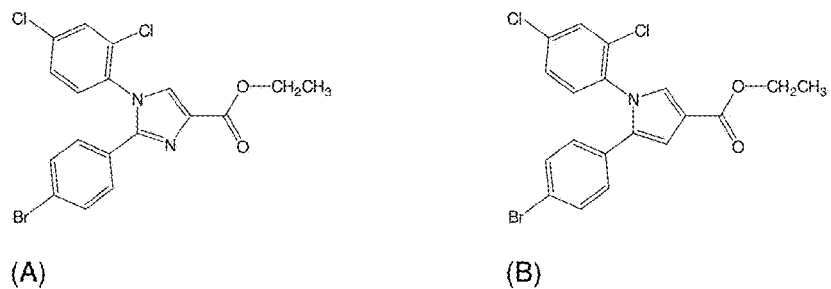
FIG. 1. (A) Prior art compound disclosed by Mascia et al. (2005) *Eur. J. Pharmacol.* 516:204-211 (designated herein as compound "TG41" or "1n"). (B) Novel compound (designated herein as compound "carbo-1n") designed to avoid inhibition of corticosteroid biosynthesis.

Anesthetics are understood to mediate at least part of their activity via modulation of the gamma-aminobutyric acid type A receptor (GABAaR). While the molecular structure of this receptor remains unknown, significant progress has been made towards understanding the interaction of the receptor with anesthetics via molecular modeling. Consensus structural alignment based on homologous templates with subsequent homology modeling reveals an intersubunit anesthetic binding cavity within the transmembrane domain of the GABAaR. As described herein, this binding site model reveals the correlation of in silico ligand docking scores with experimentally measured GABAaR potentiation for a series of propofol-like derivatives. Further screening of a series of highly potent etomidate-like derivatives also reveals a strong correlation between ligand binding scores and experimental GABAaR potentiation. However, these latter derivatives contain an exposed imidazole nitrogen which can be shown in the inventors' modeling to be capable of binding to and potentially irreversibly inhibiting the enzyme, 11-beta hydroxylase, an effect well known to occur with etomidate itself. In light of this, the inventors have created a version of the most potent of the previously-described etomidate-like derivatives in silico (containing a carbon substituted for the imidazole nitrogen, now referred to as carbo-1n). See FIG. 1B. As disclosed herein, the inventors have successfully shown in silico the inability of this compound to modify 11-beta hydroxylase despite temporary binding site occupancy, while showing strong binding scores to the anesthetic binding site within the inventors' model of the GABAaR. A further search has been made of known chemical structures for compounds having similar properties to carbo-1n. Accordingly, 12 existing compounds were identified by the inventors and subsequently successfully docked to the anesthetic binding site within the GABAaR model. These agents have been tested in tadpoles for their ability to induce the loss of righting reflex (a surrogate measure of the anesthetized state in tadpoles) and have been used in further mechanistic analyses via hippocampal slice electrophysiology. These studies have revealed a mechanism of action of the novel anesthetic agents consistent with GABAaR activity.

A new class of active anesthetic compounds has thus been identified by the inventors and described in the instant disclosure. Compounds within this class have not previously been associated with, or known to produce, anesthetic effects. These compounds are expected to provide potent clinical efficacy in producing states ranging from sedation to general anesthesia via high selectivity and affinity to receptors known to modulate consciousness. They are also expected to provide minimal cardiopulmonary perturbations, minimal to no toxicity, and kinetics favorable for rapid titratability. They are synthetically accessible with current processes or predictable new synthetic methodologies. As noted above, the currently-approved anesthetics cannot satisfy all these ideal features. Any attempt to derive a more ideal anesthetic is predicated on the identification and development of new chemical core structures that have the desired anesthetic activity in a process of scaffold hopping, as has now been demonstrated in the work provided herein.

Sophisticated molecular computations, previously only available via supercomputing facilities, can now be achieved with advanced desktop workstations. Software development has taken full advantage of high-end 3D visualization, as well as highly parallelized computational algorithms, for efficient drug screening methodologies. Concurrent with this, the inventors' understanding of the molecular substrates for conscious states has also advanced in the form of robust models of the ligand-gated ion channels that mediate particular anesthetic actions. See, for example, Bertaccini et al. (2010) *J Chem Inf Model* 50:2248-55; Murail et al. (2011) *Biophys J* 100:1642-50; Bertaccini et al. (2010) *ACS Chem. Neurosci.* 1:552-558; Bertaccini (2010) *Pharmaceuticals* 3:2178-2196; Bertaccini et al. (2010) *Anesthesiology* A1312. As presented here, this knowledge has been used to leverage the advances in computational capabilities for high throughput in silico screening (via ligand-receptor docking methodologies, fragment-based drug design, and in silico pre-clinical toxicity prediction technologies) in performing efficient lead identification and drug design using proteins that are known to bind anesthetics and/or that are involved in neuronal processes of consciousness (i.e. the inventors' current state-of-the-art molecular models of ligand-gated ion channels-LGICs).

Methods of Treatment

According to one aspect, the invention thus provides novel methods of treatment that comprise administering to a subject in need thereof a concentration of a compound sufficient to induce or maintain anesthesia in the subject. The subject anesthetic compound may be administered by any route suitable for achieving the desired effect. For example, the anesthetic may be administered orally, intravenously, inhalationally, subcutaneously, intramuscularly, transdermally, topically, or by any other suitable route.

Compounds for use in the instant methods may be represented by structural formula (I):

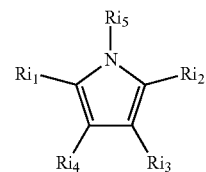

(I)

or a pharmaceutically acceptable salt thereof, wherein:
$R_{i1}$ and $R_{i2}$ are independently H, a lower alkyl group, or a phenyl group, wherein the alkyl group and phenyl group are optionally and independently substituted with alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido, and wherein two adjacent substituent groups can combine to form a ring;
either $R_{i3}$ or $R_{i4}$ is —C(O)OR$_e$, and the other group is H or a lower alkyl group;
$R_e$ is alkyl, alkenyl, alkynyl, aryl, aralkyl, heteroaryl, heteroaralkyl, cycloalkyl, cycloalkenyl, heterocyclyl, or heterocyclylalky, and is optionally substituted with alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido; and $R_{i5}$ is a phenyl group optionally substituted with alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido, and wherein two adjacent substituent groups can combine to form a ring.

In some embodiments, in the compounds of structural formula (I), either of $R_{i1}$ and $R_{i2}$ is an optionally substituted phenyl group, and the other is H or an unsubstituted lower alkyl group. In more specific embodiments, the $R_{i1}$ or $R_{i2}$ optionally substituted phenyl group is optionally substituted with an alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido group. In still more specific embodiments, the $R_{i1}$ or $R_{i2}$ optionally substituted phenyl group is optionally substituted with an alkyl, alkoxy, or halo group. In other embodiments, $R_{i1}$ and $R_{i2}$ is each independently an unsubstituted lower alkyl group.

In some embodiments, $R_e$ is an optionally substituted lower alkyl or aralkyl group, and more specifically, $R_e$ is an optionally substituted lower alkyl group.

The $R_{i5}$ phenyl group may in certain embodiments be optionally substituted with an alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido group. In specific embodiments, $R_{i5}$ is a phenyl group optionally substituted with an alkyl, alkoxy, or halo group.

In certain embodiments of the instant methods of treatment, for compounds having structural formula (I), either of $R_{i1}$ and $R_{i2}$ is a phenyl group optionally substituted with an alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido group, and the other of $R_{i1}$ and $R_{i2}$ is H or an unsubstituted lower alkyl group;

$R_e$ is an optionally substituted lower alkyl or aralkyl group; and $R_{i5}$ is a phenyl group optionally substituted with an alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido group.

In more specific method embodiments, the compound is represented by structural formula (II):

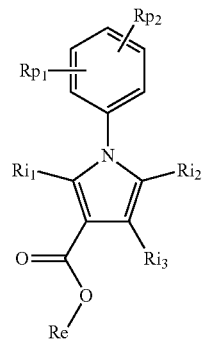

or a pharmaceutically acceptable salt thereof, wherein:

$R_{p1}$ and $R_{p2}$ are independently H, alkyl, alkenyl, alkynyl, alkoxy, alkanoyl, alkylamino, alkylthio, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido;

$R_{i3}$ is H or a lower alkyl group; and $R_{i1}$, $R_{i2}$, and $R_e$ are as defined above for structural formula (I). More specifically, $R_{p1}$ and $R_{p2}$ are independently H, alkyl, alkoxy, or halo.

In some embodiments, either of $R_{i1}$ and $R_{i2}$ is an optionally substituted phenyl group, and the other is H or an unsubstituted lower alkyl group. More specifically, the $R_{i1}$ and $R_{i2}$ optionally substituted phenyl group is substituted with an alkyl, alkoxy, or halo group.

For compounds of structural formula (II) in certain method embodiments, $R_{i1}$ and $R_{i2}$ is each independently an unsubstituted lower alkyl group. In some embodiments, $R_e$ is an optionally substituted lower alkyl or aralkyl group or is an optionally substituted lower alkyl group.

In some method embodiments, the compound is represented by structural formula (III):

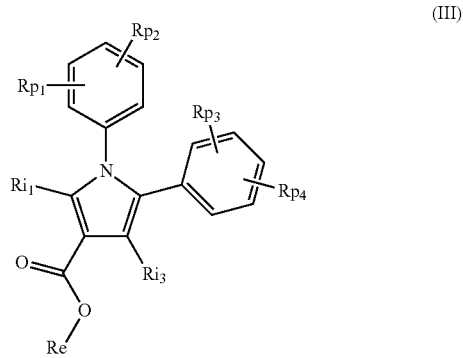

or a pharmaceutically acceptable salt thereof, wherein:

$R_{p1}$, $R_{p2}$, $R_{p3}$, and $R_{p4}$ are independently H, alkyl, alkenyl, alkynyl, alkoxy, alkanoyl, alkylamino, alkylthio, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido;

$R_{i3}$ is H or a lower alkyl group; and $R_{i1}$ and $R_e$ are as defined above for structural formula (I). Specifically, $R_{p1}$, $R_{p2}$, $R_{p3}$, and $R_{p4}$ may be independently H, alkyl, alkoxy, or halo.

In other embodiments, in the compound of structural formula (III), $R_{i1}$ is lower alkyl. In still other embodiments, $R_{i3}$ is H. In still yet other embodiments, $R_e$ is an optionally substituted lower alkyl or aralkyl group.

In the instant methods of treatment, the anesthetic compound is administered at a dose sufficient to achieve a desired anesthetic endpoint, for example amnesia, analgesia, unconsciousness, or immobility. Administered dosages for the anesthetic compound are in accordance with dosages and scheduling regimens practiced by those of skill in the art. General guidance for appropriate dosages of pharmacological agents used in the present methods is provided in *Goodman and Gilman's The Pharmacological Basis of Therapeutics*, 12th Edition (2010), and in *Physicians' Desk Reference*, $68^{th}$ Edition, each of which is hereby incorporated herein by reference.

The appropriate dosage of a particular anesthetic compound will vary according to several factors, including the chosen route of administration, the formulation of the composition, patient response, the severity of the condition, the subject's weight, the susceptibility of the subject to side effects, and the judgment of the prescribing physician. The dosage may be increased or decreased over time, as required by an individual subject. Preferred dosages for a given compound are readily determinable by those of ordinary skill in the art by a variety of means. Dosage amount and interval may be adjusted individually to provide plasma levels of the active compounds which are sufficient to maintain a desired therapeutic effect.

In one embodiment, the anesthetic compound is administered in an amount of about 1 µg to 1000 mg per dose, e.g., about 1 µg to 5 µg, about 5 µg to about 10 µg to 50 µg, about 50 µg to 100 µg, about 100 µg to 200 µg, about 200 µg to 400 µg, about 400 µg to 800 µg, about 800 µg to 1 mg, about 1 mg to 2 mg, about 2 mg to 4 mg, about 4 mg to 8 mg, about 8 mg to 10 mg, about 10 mg to 20 mg, about 20 mg to 40 mg, about 40 mg to 80 mg, about 80 mg to 100 mg, about 100 mg to 2000 mg, about 200 mg to 400 mg, about 400 mg to 1000 mg per dose, or even higher.

In another embodiment, the amount of the anesthetic compound administered per dose is determined on a per body weight basis. For example, the amount of the compound or composition per dose, as determined on a per body weight basis, may be, for example, about 10 ng/kg, about 15 ng/kg, about 20 ng/kg, about 50 ng/kg, about 100 ng/kg, about 200 ng/kg, about 500 ng/kg, about 1 µg/kg, about 2 µg/kg, about 5 µg/kg, about 10 µg/kg, about 20 µg/kg, about 50 µg/kg, about 100 µg/kg, about 200 µg/kg, about 500 µg/kg, about 1 mg/kg, about 2 mg/kg, about 5 mg/kg, about 10 mg/kg, or even higher.

In an embodiment, multiple doses of the anesthetic compound are administered. The frequency of administration of the compound may vary depending on any of a variety of factors, e.g., severity of the symptoms, and the like. For example, in an embodiment, the compound is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid). In some embodiments, for example during a surgical procedure, the compound may be administered even more frequently. For example, the compound may be administered at least once per four hours, at least once per two hours, at least once per hour, at least twice per hour, at least four times per hour, at least 10 times per hour, or even more frequently.

In some embodiments, the compound is administered continuously. The duration of administration of the anesthetic compound, e.g., the period of time over which the compound is administered, may vary, depending on any of a variety of factors, e.g., the chosen route of administration, the formulation of the composition, patient response, and so forth. For example, the compound may be administered over a period of time of at least 5 minutes, at least 30 minutes, at least one hour, at least 2 hours, at least 4 hours, at least 8 hours, at least one day, at least one week, or even longer. In other embodiments, the compound may be administered over a period of time of no more than one week, no more than one day, no more than 8 hours, no more than 4 hours, no more than 2 hours, no more than one hour, no more than 30 minutes, no more than 5 minutes, or even shorter. In some embodiments, the compound may be administered for a time period of about 5 minutes to 30 minutes, of about 30 minutes to one hour, of about one hour to 2 hours, of about 2 hours to 4 hours, of about 4 hours to 8 hours, of about 8 hours to one day, or of about one day to one week.

In various embodiments, the anesthetic compounds are delivered to the subject via the respiratory pathway, e.g., via inhalational, pulmonary and/or intranasal delivery. Technologies and devices for inhalational anesthetic drug dosing are known in the art. They are described, for example, in *Miller's Anesthesia* (2009), edited by Ronald D. Miller, et al., 2 vols, 7th ed, Philadelphia, Pa., Churchill Livingstone/Elsevier. In one embodiment, the anesthetic compounds are administered to deliver a dose of between about 0.1-10.0 percent of 1 atmosphere (1 atm), e.g., 0.5-5.0 percent of 1 atm, e.g., about 1.0-3.5 of 1 atm, e.g., about 0.1, 0.2, 0.3, 0.4. 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 or 10.0 percent of 1 atm, e.g., delivered over the period of time of desired anesthesia. The dose used will be dependent upon the drug potency, and the compound or mixture of compounds administered.

Detailed information about the delivery of therapeutically active anesthetic agents in the form of vapors or gases is available in the art. The anesthetic compound will typically be vaporized using a vaporizer using a carrier gas such as oxygen, air, or helium, or a mixture thereof, to achieve a desired concentration suitable for inhalation by use of a semi-open or semi-closed anesthetic circuit, as is known to those of ordinary skill in the art. The anesthetic compound, in gaseous form, may also be directly mixed with a carrier gas such as oxygen, air, or helium, or a mixture thereof, to achieve a desired concentration suitable for inhalation by use of a semi-open or semi-closed anesthetic circuit, as is understood by the skilled artisan. The anesthetic compound may also be administered by direct application onto or through a breathing mask, also termed an open circuit. In animal subjects, the compound may also be administered into a closed chamber or container containing the animal subject whereby the compound is delivered by the respiratory tract as the animal breathes, as is known to those of ordinary skill in the art.

In some aspects of the invention, the anesthetic compound or mixture of compounds, is dissolved or suspended in a suitable solvent, such as water, ethanol, or saline, and administered by nebulization. A nebulizer produces an aerosol of fine particles by breaking a fluid into fine droplets and dispersing them into a flowing stream of gas. Medical nebulizers are designed to convert water or aqueous solutions or colloidal suspensions to aerosols of fine, inhalable droplets that can enter the lungs of a subject during inhalation and deposit on the surface of the respiratory airways. Typical pneumatic (compressed gas) medical nebulizers develop approximately 15 to 30 microliters of aerosol per liter of gas in finely divided droplets with volume or mass median diameters in the respirable range of 2 to 4 micrometers. Predominantly, water or saline solutions are used with low solute concentrations, typically ranging from 1.0 to 5.0 mg/mL.

Nebulizers for delivering an aerosolized solution to the lungs are commercially available from a number of sources, including the AERx™ (Aradigm Corp., Hayward, Calif.) and the Acorn II® (Vital Signs Inc., Totowa, N.J.).

Metered dose inhalers are also known and available. Breath-actuated inhalers typically contain a pressurized propellant and provide a metered dose automatically when the patient's inspiratory effort either moves a mechanical lever or the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978; and 4,896,832.

In various other embodiments, the anesthetic compounds of the instant disclosure are delivered to the subject via injection. The compounds are preferably formulated, as described below, in compositions that facilitate the effective delivery of the injected compounds to the nervous system. In particular, and as described below, the compositions are preferably delivered in the instant methods of treatment by parenteral administration, as is well understood in the art.

In some embodiments, the present invention provides methods of treatment that induce or maintain tranquilization or sedation in a subject. For example, seriously ill subjects, such as patients in an intensive care unit, may be sedated according to the instant methods, for example by continuous infusion of a solution comprising one or more of the instant anesthetic compounds. In more specific embodiments, the methods induce or maintain tranquilization in a subject. In some other embodiments, the methods induce or maintain amnesia in a subject. Typically, the amount of a compound that is required to induce or maintain amnesia in a subject is larger than the amount required to induce or maintain tranquilization in the subject. In yet other embodiments, the invention provides methods to induce or maintain a hypnotic state in a subject. Typically, the amount of an anesthetic compound that is required to induce or maintain a hypnotic state in a subject is larger than the amount required to induce or maintain amnesia in the subject. In still other embodiments, the invention provides methods that induce or maintain a state of insensitivity to noxious stimulation in a subject. Typically, the amount of an anesthetic compound that is required to induce or maintain a state of insensitivity to noxious stimulation in a subject is larger than the amount required to induce or maintain a hypnotic state in the subject.

The present invention includes methods of inducing or maintaining a spectrum of states of anesthesia in a subject as a function of the administered dosage of an anesthetic compound disclosed herein. In some embodiments, the methods include administering low dosages of a compound to induce or maintain tranquilization or sedation in a subject. In some other embodiments, the methods include administering higher dosages than that required to induce or maintain tranquilization of a compound or a mixture of compounds which are described herein to induce amnesia in a subject. In yet other embodiments, the methods include administering even higher dosages than that required to induce amnesia in a subject of a compound or a mixture of compounds which are described herein to induce a hypnotic state in a subject. In still other embodiments, the methods include administering yet even higher dosages than that required to induce a hypnotic state in a subject of a compound or a mixture of compounds which are described herein to induce a state of insensitivity to noxious stimulation in a subject.

In some embodiments, the present invention provides methods of treatment of pain in a subject. In some pain treatment embodiments, the anesthetic compound is delivered topically. In other pain treatment embodiments, the anesthetic compound is delivered systemically.

Compounds

According to another aspect of the invention, novel compounds are provided that display anesthetic effects on animal subjects. A first category of compounds is represented by structural formula (II):

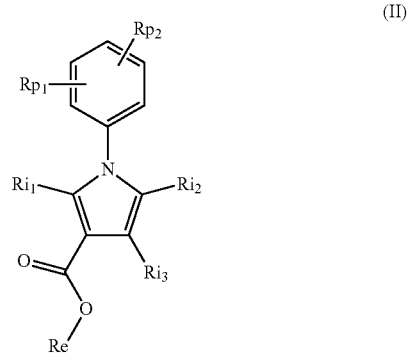

(II)

or a pharmaceutically acceptable salt thereof, wherein:
$R_{p1}$ and $R_{p2}$ are independently H, alkyl, alkenyl, alkynyl, alkoxy, alkanoyl, alkylamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, alkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, or azido, each of which may be optionally substituted where chemically feasible;
$R_{i1}$ is H or a $C_1$-$C_6$ alkyl group;
$R_{i2}$ is a phenyl group optionally substituted with one or more alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido groups, and wherein two adjacent substituent groups can combine to form a ring;

$R_{i3}$ is H or an unsubstituted lower alkyl group; and $R_e$ is $C_3$-$C_8$-alkyl, alkenyl, alkynyl, aryl, aralkyl, heteroaryl, heteroaralkyl, cycloalkyl, cycloalkenyl, heterocyclyl, or heterocyclylalky, and is optionally substituted with alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, or azido;

provided that when $R_{i1}$ is methyl, $R_{i2}$ is unsubstituted phenyl, and $R_e$ is benzyl, isopropyl, isobutyl, t-butyl, methoxyethyl, or 4,4-difluoro-3-methyl-3-buten-1-yl, and $R_{p1}$ is H, then $R_{p2}$ is not H;

when $R_{i1}$ is methyl, $R_{i2}$ is 2-methoxyphenyl, $R_e$ is t-butyl, and $R_{p1}$ is H, then $R_{p2}$ is not H, 3-amino, 3-azido, 4-bromo, or 4-nitro; and when $R_{i1}$ is methyl, $R_{i2}$ is 2-methoxyphenyl, $R_e$ is benzyl, and $R_{p1}$ is H, then $R_{p2}$ is not H.

As used herein, the term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In some embodiments, a straight chain or branched chain alkyl has 30 or fewer carbon atoms in its backbone (e.g., $C_1$-$C_{30}$ for straight chains, $C_3$-$C_{30}$ for branched or cyclic chains), more specifically 20 or fewer carbon atoms in its backbone (e.g., $C_1$-$C_{20}$ for straight chains, $C_3$-$C_{20}$ for branched or cyclic chains), and even more specifically 10 or fewer carbon atoms in its backbone (e.g., $C_1$-$C_{10}$ for straight chains, $C_3$-$C_{10}$ for branched or cyclic chains). Likewise, some cycloalkyls have from 3-10 carbon atoms in their ring structure, and more specifically have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents may include, for example, a halo, a hydroxyl, a carbonyl (such as a keto, a carboxy, an alkoxycarbonyl, a formyl, an acyl, a carbonate, a carbamate, an ester, or a urea), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a thio, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN, halo, and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, halo, and the like.

As used herein, the term "alkoxy" refers to an oxy group substituted with an alkyl group, in certain specific embodiments, a lower alkyl group. Representative alkoxy groups include methoxy, ethoxy, propoxy, t-butoxy, and the like.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed above, except where stability is prohibitive. For example, substitution of alkenyl groups by one or more alkyl, cycloalkyl, heterocyclyl, aryl, or heteroaryl groups is contemplated.

The term "$C_{x-y}$" when used in conjunction with a chemical moiety, such as acyl, acyloxy, alkyl, alkenyl, alkynyl, or alkoxy, is meant to include groups that contain from x to y carbons in the chain. For example, the term "$C_{x-y}$-alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. "$C_0$-alkyl" indicates a hydrogen where the group is in a terminal position, or is a bond if internal. The terms "$C_{2-y}$-alkenyl" and "$C_{2-y}$-alkynyl" refer to substituted or unsubstituted unsaturated aliphatic groups analogous in length and possible substitution to the alkyls described above, but that contain at least one double or triple bond, respectively.

The term "alkylamino", as used herein, refers to an amino group substituted with at least one alkyl group.

The term "alkylthio", as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, cycloalkyl, heterocyclyl, aryl, or heteroaryl groups is contemplated.

The term "amide" or "amido", as used herein, refers to a group

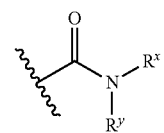

wherein $R^x$ and $R^y$ each independently represent a hydrogen or hydrocarbyl group, or $R^x$ and $R^y$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

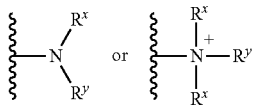

wherein $R^x$, $R^y$, and $R^z$ each independently represent a hydrogen or a hydrocarbyl group, or $R^x$ and $R^y$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein includes substituted or unsubstituted single-ring aromatic groups in which each atom of the ring is carbon. In certain embodiments, the ring is a 5- to 7-membered ring, and in more specific embodiments is a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

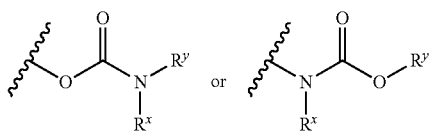

wherein $R^x$ and $R^y$ independently represent hydrogen or a hydrocarbyl group, or $R^x$ and $R^y$ taken together with the atoms to which they are attached complete a heterocycle having from 4 to 8 atoms in the ring structure.

The term "cycloalkyl", as used herein, refers to a non-aromatic saturated or unsaturated ring in which each atom of the ring is carbon. In certain embodiments, a cycloalkyl ring contains from 3 to 10 atoms, and in more specific embodiments from 5 to 7 atoms.

The term "carbonate" is art-recognized and refers to a group —OCO$_2$—$R^x$, wherein $R^x$ represents a hydrocarbyl group.

The term "carboxy", as used herein, refers to a group represented by the formula —CO$_2$H.

The term "ester", as used herein, refers to a group —C(O)OR$^x$ wherein $R^x$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The term "guanidinyl" is art-recognized and may be represented by the general formula

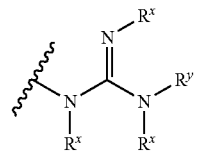

wherein $R^x$ and $R^y$ independently represent hydrogen or a hydrocarbyl.

The terms "halo" and "halogen" as used herein mean halogen and include chloro, fluoro, bromo, and iodo.

The terms "hetaralkyl" and "heteroaralkyl", as used herein, refer to an alkyl group substituted with a hetaryl group.

The terms "heteroaryl" and "hetaryl" include substituted or unsubstituted aromatic single ring structures, in certain specific embodiments 5- to 7-membered rings, more specifically 5- to 6-membered rings, whose ring structures include at least one heteroatom, in some embodiments one to four heteroatoms, and in more specific embodiments one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Typical heteroatoms are nitrogen, oxygen, and sulfur.

The terms "heterocyclyl", "heterocycle", and "heterocyclic" refer to substituted or unsubstituted non-aromatic ring structures, in certain specific embodiments 3- to 10-membered rings, more specifically 3- to 7-membered rings, whose ring structures include at least one heteroatom, in some embodiments one to four heteroatoms, and in more specific embodiments one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes herein, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, and in certain embodiments, six or fewer. A "lower alkyl", for example, refers to an alkyl group that contains ten or fewer carbon atoms, and in specific embodiments six or fewer carbon atoms. In certain embodiments, the acyl, acyloxy, alkyl, alkenyl, alkynyl, and alkoxy substituents defined herein are respectively lower acyl, lower acyloxy, lower alkyl, lower alkenyl, lower alkynyl, and lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, more specifically from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc., under conditions in which the compound is to be used. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents may include any substituents described herein, for example, a halogen, a hydroxyl, a carbonyl (such as a keto, a carboxy, an alkoxycarbonyl, a formyl, an acyl, a carbonate, a carbamate, an ester, or a urea), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate.

Unless specifically described as "unsubstituted", references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

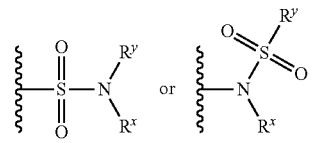

wherein R$^x$ and R$^y$ independently represent hydrogen or hydrocarbyl.

The term "sulfoxide" is art-recognized and refers to the group —S(O)—R$^x$, wherein R$^x$ represents a hydrocarbyl.

The term "sulfonate" is art-recognized and refers to the group —SO$_3$H, or a pharmaceutically acceptable salt thereof.

The term "sulfone" is art-recognized and refers to the group —S(O)$_2$—R$^x$, wherein R$^x$ represents a hydrocarbyl.

The term "thioalkyl", as used herein, refers to an alkyl group substituted with a thiol group.

The term "thioester", as used herein, refers to a group —C(O)SR$^x$ or —SC(O)R$^x$ wherein R$^x$ represents a hydrocarbyl.

The term "thioether", as used herein, is equivalent to an ether, wherein the oxygen is replaced with a sulfur.

The term "urea" is art-recognized and may be represented by the general formula

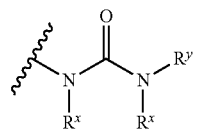

wherein R$^x$ and R$^y$ independently represent hydrogen or a hydrocarbyl.

It should be understood that some of the compounds of the invention may contain one or more stereocenters, and that, absent an explicit indication otherwise, compounds containing only one or the other stereoisomer at the stereocenter, or a mixture of the stereoisomers, in any combination, are considered within the scope of the invention. For example, the compounds of the invention may be pure enantiomeric or diastereomeric forms of a given molecule or may be mixtures of the enantiomeric or diastereomic forms, at any ratio.

In some embodiments of the above category of compounds, R$_{i2}$ is a phenyl group optionally substituted with one or more alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido groups. In specific embodiments, R$_{i2}$ is a phenyl group optionally substituted with one or more alkyl, alkoxy, or halo groups.

In some embodiments, R$_e$ is an optionally substituted C$_3$-C$_8$-alkyl or aralkyl group, or R$_e$ is an optionally substituted C$_3$-C$_8$-alkyl group.

In some embodiments, R$_{p1}$ and R$_{p2}$ are independently H, alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido. In specific embodiments, $R_{p1}$ and $R_{p2}$ are independently H, alkyl, alkoxy, or halo.

A second category of compounds is represented by structural formula (II), or a pharmaceutically acceptable salt thereof, wherein:

$R_{p1}$ and $R_{p2}$ are independently H, alkyl, alkenyl, alkynyl, alkoxy, alkanoyl, alkylamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, alkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, or azido, each of which may be optionally substituted where chemically feasible;

$R_{i1}$ is H or a $C_1$-$C_6$ alkyl group;

$R_{i2}$ is a phenyl group substituted with one or more alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido groups, and wherein two adjacent substituent groups can combine to form a ring;

$R_{i3}$ is H or an unsubstituted lower alkyl group; and $R_e$ is alkyl, alkenyl, alkynyl, aryl, aralkyl, heteroaryl, heteroaralkyl, cycloalkyl, cycloalkenyl, heterocyclyl, or heterocyclylalky, and is optionally substituted with alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, or azido;

provided that $R_{i2}$ is not 2-aminophenyl, 3-aminophenyl, 3-amino-4-hydroxyphenyl, 4-aminophenyl, 3-azidophenyl, 1,1'-biphenyl, 2-bromophenyl, 3-bromophenyl, 4-bromophenyl, 2-carboxyphenyl, 2-(chlorocarbonyl)phenyl, 4-chlorophenyl, 2,4-dichlorophenyl, 2,4-dimethoxyphenyl, 3,4-dimethoxyphenyl, 3,4-dimethylphenyl, 4-fluorophenyl, 2-methoxyphenyl, 3-methoxyphenyl, 4-methoxyphenyl, 3-(ethoxycarbonyl)phenyl, 4-(methoxycarbonyl)phenyl, 2-methylphenyl, 4-methylphenyl, 4-(methylsulfonyl)phenyl, 4-(methylthio)phenyl, 3-(4-morpholinylsulfonyl)phenyl, 2-nitrophenyl, 3-nitrophenyl, 4-nitrophenyl, 3-(phenylamino)phenyl, 4-(1H-pyrrol-1-yl)phenyl, 4-(1-methyl-1H-pyrazol-4-yl)phenyl, 2-hydroxy-5-aminophenyl, or 4-[5-(4-chlorophenyl)-3-(ethoxycarbonyl)-2-methyl-1H-pyrrol-1-yl]phenyl].

In more specific embodiments of this category, $R_{i2}$ is a phenyl group substituted with one or more alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido groups. Even more specifically, $R_{i2}$ is a phenyl group substituted with one or more alkyl, alkoxy, or halo groups.

In other more specific embodiments, $R_e$ is an optionally substituted lower alkyl or aralkyl group or $R_e$ is an optionally substituted lower alkyl group.

In still other more specific embodiments, $R_{p1}$ and $R_{p2}$ are independently H, alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido, or $R_{p1}$ and $R_{p2}$ are independently H, alkyl, alkoxy, or halo.

A third category of compounds is represented by structural formula (IV):

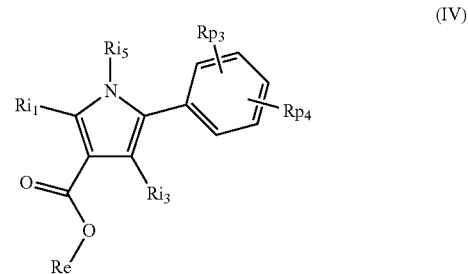

(IV)

or a pharmaceutically acceptable salt thereof, wherein:

$R_{p3}$ and $R_{p4}$ are independently H, alkyl, alkenyl, alkynyl, alkoxy, alkanoyl, alkylamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, alkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, or azido, each of which may be optionally substituted where chemically feasible;

$R_{i1}$ is H or a $C_1$-$C_6$ alkyl group;

$R_{i5}$ is a phenyl group substituted with one or more alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido groups;

$R_{i3}$ is H or an unsubstituted lower alkyl group; and $R_e$ is alkyl, alkenyl, alkynyl, aryl, aralkyl, heteroaryl, heteroaralkyl, cycloalkyl, cycloalkenyl, heterocyclyl, or heterocyclylalky, and is optionally substituted with alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, or azido;

provided that $R_{i5}$ is not 2-aminophenyl, 2-bromophenyl, 2-carboxyphenyl, 2-chlorophenyl, 2-(dimethylamino) phenyl, 2-ethylphenyl, 2-hydroxyphenyl, 2-methoxyphenyl, 2-methylphenyl, 2-nitrophenyl, 2-trifluoromethylphenyl, 3-acetylphenyl, 3-aminophenyl, 3-aminocarbonylphenyl, 3-azidophenyl, 3-bromophenyl, 3-butoxyphenyl, 3-carboxyphenyl, 3-chlorophenyl, 3-(dimethylamino)phenyl, 3-fluorophenyl, 3-hydroxylphenyl, 3-iodophenyl, 3-methoxyphenyl, 3-methylphenyl, 3-methylthiophenyl, 3-nitrophenyl, 3-trifluoromethylphenyl, 4-aminophenyl, 4-azidophenyl, 4-bromophenyl, 4-carboxyphenyl, 4-chlorophenyl, 4-ethoxyphenyl, 4-ethylphenyl, 4-fluorophenyl, 4-hydroxyphenyl, 4-methoxyphenyl, 4-methylphenyl, 4-nitrophenyl, 4-trifluoromethoxyphenyl, 4-(3,3,3-trifluoropropoxy)phenyl, 2,4-difluorophenyl, 2,4-dichlorophenyl, 3-amino-4-hydroxyphenyl, 3-carboxy-4-hydroxyphenyl, 2-hydroxy-5-aminophenyl, 2-bromo-4-acetylphenyl, 2,4-dibromophenyl, 2-bromo-4-(ethoxycarbonyl)phenyl, 2-bromo-4-fluorophenyl, 2-bromo-4-trifluoromethylphenyl, 3-hydroxy-4-carboxyphenyl, 3-carboxy-4-hydroxyphenyl, 2,6-diisopropylphenyl, 2,5-dimethoxyphenyl, 3,4-dimethoxyphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methoxy-4-methylphenyl, 2-methyl-3-chlorophenyl, 2,4-dichlorophenyl, 3,4-dichlorophenyl, 3,5-dichlorophenyl, 2-methoxy-5-nitrophenyl, 2-nitro-4-methylphenyl, or 2-chloro-5-trifluoromethylphenyl.

In more specific embodiments of this category, $R_{i5}$ is a phenyl group optionally substituted with one or more alkyl, alkoxy, or halo groups.

In other more specific embodiments, $R_e$ is an optionally substituted lower alkyl or aralkyl group, or $R_e$ is an optionally substituted lower alkyl group.

In still other more specific embodiments, $R_{p3}$ and $R_{p4}$ are independently H, alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido. Even more specifically, $R_{p3}$ and $R_{p4}$ are independently H, alkyl, alkoxy, or halo.

A fourth category of compounds is represented by structural formula (II):

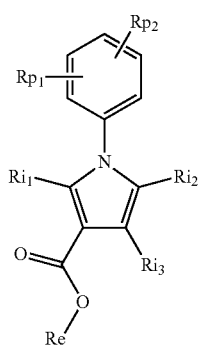

(II)

or a pharmaceutically acceptable salt thereof, wherein:
$R_{p1}$ and $R_{p2}$ are independently H, alkyl, alkenyl, alkynyl, alkoxy, alkanoyl, alkylamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, alkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, or azido, each of which may be optionally substituted where chemically feasible;

$R_{i1}$ is H;

$R_{i2}$ is a phenyl group optionally substituted with one or more alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido groups, and wherein two adjacent substituent groups can combine to form a ring;

$R_{i3}$ is H or an unsubstituted lower alkyl group; and $R_e$ is alkyl, alkenyl, alkynyl, aryl, aralkyl, heteroaryl, heteroaralkyl, cycloalkyl, cycloalkenyl, heterocyclyl, or heterocyclylalky, and is optionally substituted with alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, or azido;

provided that
when $R_{i2}$ is 4-(methylsulfonyl)phenyl, $R_e$ is methyl, and $R_{p1}$ is H, then $R_{p2}$ is not 4-fluoro; and
when $R_{i2}$ is unsubstituted phenyl, $R_e$ is methyl, and $R_{p1}$ is H, then $R_{p2}$ is not 4-methoxy.

In more specific embodiments of this category, $R_{i2}$ is a phenyl group optionally substituted with one or more alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido groups.

In still more specific embodiments, $R_{i2}$ is a phenyl group optionally substituted with one or more alkyl, alkoxy, or halo groups.

In some embodiments, $R_e$ is an optionally substituted lower alkyl or aralkyl group or is an optionally substituted lower alkyl group.

In some embodiments, $R_{p1}$ and $R_{p2}$ are independently H, alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido.

In specific embodiments, $R_{p1}$ and $R_{p2}$ are independently H, alkyl, alkoxy, or halo.

Pharmaceutical Compositions

In another aspect, the instant invention provides pharmaceutical compositions comprising a compound of the invention and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil, injectable organic esters, lipid emulsions such as intralipid and the like, and other suitable carriers. In a specific embodiment, when such pharmaceutical compositions are for human administration, the aqueous solution is pyrogen free, or substantially pyrogen free. The excipients may be chosen, for example, to effect delayed release of an agent or to selectively target one or more cells, tissues or organs. The pharmaceutical composition may be in dosage unit form such as tablet, capsule, sprinkle capsule, granule, powder, syrup, suppository, injection or the like. The composition may also be present in a transdermal delivery system, e.g., a skin patch.

A pharmaceutically acceptable carrier may contain physiologically acceptable agents that act, for example, to stabilize or to increase the absorption of a compound of the instant invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The pharmaceutical composition also may comprise a liposome or other polymer matrix, which may have incorporated therein, for example, a compound of the invention. Liposomes, for example, which consist of phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent, or encapsulating material, involved in carrying or transporting the subject compounds from one organ, or portion of the body, to another organ, or portion of the body. Each carrier must be "acceptable" in the sense of being compatible with the other ingredients of the formulation and not injurious to the patient. Some examples of materials that can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. See Remington: The Science and Practice of Pharmacy, 20th ed. (Alfonso R. Gennaro ed.), 2000.

A pharmaceutical composition containing a compound of the instant invention may be administered to a subject by any of a number of routes of administration including, for example, orally (for example, drenches as in aqueous or non-aqueous solutions or suspensions, tablets, boluses, powders, granules, pastes for application to the tongue); sublingually; anally, rectally, or vaginally (for example, as a pessary, cream, or foam); parenterally (including intramuscularly, intravenously, subcutaneously, or intrathecally as, for example, a sterile solution or suspension); nasally; intraperitoneally; subcutaneously; transdermally (for example as a patch applied to the skin); or topically (for example, as a cream, ointment or spray applied to the skin). The compound may also be formulated for inhalation. In certain embodiments, a compound of the instant invention may be simply dissolved or suspended in sterile water. Details of appropriate routes of administration and compositions suitable for same can be found in, for example, U.S. Pat. Nos. 6,110,973; 5,763,493; 5,731,000; 5,541,231; 5,427,798; 5,358,970; and 4,172,896, as well as in patents cited therein.

The formulations of the present invention may conveniently be presented in unit dosage form and may be prepared by any methods well known in the art of pharmacy. The amount of active ingredient that may be combined with a carrier material to produce a single dosage form will vary depending upon the subject being treated and the particular mode of administration. The amount of active ingredient that may be combined with a carrier material to produce a single dosage form will generally be that amount of the compound that produces a therapeutic effect. Generally, out of one hundred percent, this amount will range from about 0.1 percent to about 50 percent of active ingredient, in some embodiments from about 0.2 percent to about 10 percent, and in more specific embodiments from about 0.5 percent to about 2 percent. For example, compounds of the present disclosure may be formulated in a unit dose form between about 1 µg and 1000 mg. In some embodiments, compounds or compositions of the present disclosure may be formulated in a unit dose of about 1 µg to 20 µg, of about 20 µg to 1 mg, of about 1 mg to 10 mg, of about 10 mg to 100 mg, and of about 50 mg to 500 mg. In particular, an embodiment including a compound may be formulated in 0.1 µg, 0.2 µg, 0.5 µg, 1 µg, 20 µg, 50 µg, 100 µg, 200 µg, 500 µg, 1 mg, 2 mg, 5 mg, 10 mg, 20 mg, 50 mg, 100 mg, 200 mg, and 500 mg unit dose form.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary, or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that may be used include polymeric substances and waxes. The active ingredient may also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions may also include adjuvants such as wetting agents, emulsifying and suspending agents, sweetening, flavoring, coloring, perfuming, and preservative agents.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

Pharmaceutical compositions of this invention suitable for parenteral administration comprise one or more compounds of the invention in combination with one or more pharmaceutically acceptable sterile isotonic aqueous or nonaqueous solutions, dispersions, suspensions, or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, injectable organic esters, such as ethyl oleate, and lipid emulsions, such as Intralipid and the like. Proper fluidity may be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, chelators and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release may be controlled. Examples of other biodegradable polymers include poly(orthoesters) and poly(anhydrides). Depot injectable formulations are also prepared by entrapping the drug in liposomes or microemulsions that are compatible with body tissue.

Methods of introduction may also be provided by rechargeable or biodegradable devices. Various slow release polymeric devices have been developed and tested in vivo in recent years for the controlled delivery of drugs. A variety of biocompatible polymers (including hydrogels), including both biodegradable and non-degradable polymers, may be used to form an implant for the sustained release of a compound at a particular target site.

Anesthetic compounds, including the compounds of the instant disclosure, often display limited solubility in aqueous solution, and they are therefore preferably formulated with one or more agents that increase their solubility in water. Examples of such agents include surfactants and lipid emulsions, or other similar solubilizing agents, and the compositions may include one or more additional solvents. Alternatively, the compositions may include an additional water-miscible, non-aqueous solvent, provided in sufficient concentration in the aqueous solution to obtain a homogeneous composition. In yet another alternative, the compositions may include an oil-in-water emulsion in which the instant anesthetic compound, either alone or dissolved in a water-immiscible solvent, for example, an oil, is emulsified with water by means of a surfactant. Suitable surfactants and other solubilizing agents are well known in the art, for example, the surfactants described for use in formulating propofol and etomidate. See, e.g., U.S. Pat. Nos. 4,056,635; 4,289,783; 4,798,846; 5,731,355; 5,858,410; 7,915,317; 8,383,687; 8,796,340, the disclosures of which are hereby incorporated by reference herein in their entireties. Such agents include without limitation, oils, lipids, polyols, and the like, in any combination and ratio. As noted above, the formulations optionally contain additional agents, such as anti-microbial agents and the like.

In another aspect, the invention is provided substantially as described in any part of the instant disclosure, including the examples, in any combination, and as shown in the accompanying drawings.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

Molecular Modeling and Testing of Compounds as Novel Anesthetic Agents

Materials and Methods:

1. Homologous Template Identification and Analyses

The cryo-electron microscopy-derived structure of the alpha 1 subunit from the torpedo nicotinic acetylcholine receptor (nAChR, PDB ID 2BG9) (Unwin (2005) *J Mol Biol* 346:967-89), the NMR derived, transmembrane domain structures of the alpha 4 and beta 2 subunits of the nAChR (PDB ID 2LLY, 2LM2) (Bondarenko et al. (2012) *Biochim Biophys Acta* 1818:1261-8), and the crystallographically derived structures of the eukaryotic glutamate-gated chloride channel (GluCl, PDB ID 3RIF, 3RHW) (Hibbs et al. (2011) *Nature* 474:54-60), as well as the prokaryotic pH sensing channels, Gloeobacter violaceus ion channel (GLIC, PDB ID 3EAM) (Corringer et al. (2009) *J Physiol* 588:565-72; Bocquet et al. (2009) *Nature* 457:111-4), and Erwinia chrysanthemi ion channel (ELIC, PDB ID 2VL0) (Hilf et al. (2008) *Nature* 452:375-9) were downloaded from the Research Collaboratory for Structural Biology (RCSB) protein databank. Most of the calculations below were performed with algorithms present within the Discovery Studio 3.1 software suite (Accelrys, San Diego, Calif.) except where noted. Multiple structure alignments were separately performed via the SAlign (Braberg et al. (2012) *Bioinformatics* 28:2072-3) and 3DMA algorithms. A multiple sequence alignment profile was then derived from these structural alignments. The sequences of the individual subunits for the mouse GABAaR were downloaded from the National Center for Biotechnology Institute (NCBI). They were concatenated and arranged in the clockwise order (as viewed from the extracellular side of the channel) gamma 2, alpha 1, beta 3, alpha 1, beta 3 in accordance with knowledge in the art. See Trudell (2002) *Biochim Biophys Acta* 1565:91-6; Sigel et al. (2012) *J Biol Chem* 287:40224-31; Baur et al. (2006) *FEBS Lett* 580:1616-20; Baumann et al. (2002) *J Biol Chem* 277:46020-5; Tretter (1997) *J Neurosci* 17:2728-37. These works demonstrate the appropriate stoichiometry and arrangement of subunit subtypes so as to satisfy a variety of mutational results required for specific ligand binding in the extracellular domain of the GABAaR. See Cromer et al. (2002) *Trends Biochem Sci* 27:280-7; Baur et al. (2010) *J Neurochem* 115:1478-85. The sequences of the mouse GABAaR alpha 1, beta 3 and gamma 2 subunits were then aligned with the previously derived sequence of the known structural template (GluCl) using the Align123 algorithm, a version of the ClustalW routine. Higgins et al. (1996) *Methods Enzymol* 266:383-402.

2. Model Construction using the Modeller Algorithm

The GluCl structural coordinates were utilized as the template for homology modeling for the reasons reviewed in the Discussion section below. For the GluCl template, the native glutamate ligand, which was located in the intersubunit cleft within the extracellular domain, and the ivermectin located in the intersubunit cleft in the transmembrane domain, were removed. The Modeller (Eswar et al. (2008) *Methods Mol Biol* 426:145-59) algorithm was used for assignment of coordinates for aligned amino acids. Modeller implements comparative protein structure modeling by satisfaction of spatial restraints that are obtained from the set of structural templates, thereby generating a probability density function governing the way in which heavy atom coordinates are assigned. Routines implemented within the Modeller framework also allow the construction and optimization of loops of amino acids for which no template coordinates can be assigned, and the initial refinement of amino acid sidechains. Final rotamer search optimization was performed using the ChiRotor routine within Discovery Studio.

3. Docking to an Anesthetic Binding Site and Quantifying the Interaction:

As in the inventors' previous work (Bertaccini et al. (2010) *J Chem Inf Model* 50:2248-55), the binding sites were identified by the convergence of residues relevant to anesthetic modulation on a common transmembrane intersubunit location in three dimensional space. The volume of the initial binding site was very small due to the aforementioned energy optimizations and the rotation of amino acid sidechains into the binding site. Therefore, a single propofol molecule was manually inserted into one of the two putative binding sites between alpha and beta subunits within the model built using Modeller. This propofol was optimized into position using molecular mechanics with the CHARMm force field, followed by molecular dynamics (Brooks et al. (2009) *J Comput Chem* 30:1545-614), while allowing for sidechain flexibility with only backbone atoms fixed. While the work of Mihic et al. has demonstrated that occupancy of only one binding site is sufficient to enhance the homologous glycine receptor's function (Roberts et al. (2006) *J Biol Chem* 281:3305-11), the work of Forman et al. (Forman et al. (2012) *Curr Opin Anaesthesiol* 25:411-8; Forman et al. (2011) *Can J Anaesth* 58:191-205; Ruesch et al. (2012) *Anesthesiology* 116:47-55; Stewart et al. (2013) *Mol Pharmacol* 83:1200-08) shows that propofol's enhancing action in GABAaR requires occupancy of perhaps three propofol sites. For the sake of computational simplicity here and since both binding sites are identical in amino acid contribution and location between alpha and beta subunits, only one transmembrane binding site was chosen for docking examinations. The CDocker algorithm (Wu et al. (2003) *J Comput Chem* 24:1549-62) was then used to randomly dock a congeneric series of flexible propofol derivatives, as well as propofol itself, into a rigid binding pocket and score their best relative binding affinities for correlation with known GABAaR potentiation EC50's. CDOCKER is an implementation of a CHARMm molecular mechanics-based docking tool using a rigid receptor. This method begins by generating a set of 10 ligand conformations using 1000 steps of high-temperature (1000 K) molecular dynamics with different random seeds and includes electrostatic interactions. Random pose orientations of the conformations were produced by translating the center of the ligand to a specified location within a predefined sphere incorporating the receptor site, and performing a series of random rotations. The sphere in this case was chosen as a 7 angstrom radius from the center of mass of the initial manually docked propofol pose. This was done in an effort to both center the region of docking exploration within the area of relevant residues as well as to have a large enough radius to allow adequate random placement about these residues. A softened (temporarily reduced van der Waals radii) energy was calculated and the orientation kept if the energy was less than a specified threshold (300 kcal/mol). This process continued until either the desired number of low-energy orientations was found (set at 10), or the maximum number of bad orientations were tried (set at 800). Each orientation was subjected to simulated annealing molecular dynamics. The temperature was heated to a high enough level (700 K over 2000 steps) to overcome local energy barriers between adjacent minima and then cooled to the target temperature (300 K over 5000 steps). A final minimization of the ligand in the rigid receptor using a non-softened full potential (including full van der Waals radii and electrostatics) was performed. For each final pose, the CDOCKER score energy (interaction energy plus ligand strain) and the CDOCKER interaction score alone were calculated. The poses were sorted and the top scoring (most negative, thus favorable to binding) poses were retained. For performance, many of these steps used a nonbonded energy grid, rather than the full potential energy terms usually used by CHARMm. This choice can provide a significant time saving during large database screening, but was reverted to its fully explicit CHARMm form during final optimizations to avoid the loss of some initial accuracy associated with the initial grid-based search.

The compounds with agonist activity that were docked included propofol (2,6-diisopropylphenol); 2,6-dimethylphenol; phenol; 2,6-diethylphenol; 2-isopropylphenol; 2,6-disecbutylphenol. This is the same series of propofol analogs studied by Eckenhoff and colleagues for their correlation of binding free energy to horse spleen apoferritin derived from isothermal titration calorimetry with experimentally derived EC50 for GABAaR potentiation. Vedula et al. (2009) *J Biol Chem* 284:24176-84; Krasowski et al. (2001) *J Pharmacol Exp Ther* 297:338-51. These compounds were specifically chosen for the instant docking studies as they are the only propofol derivatives which also have experimentally derived specific binding constants to horse spleen apoferritin. It is the latter which were initially and reliably reproduced with the CDocker methodologies as a means of method validation specific to this set of compounds (unpublished data). Finally, as inactive controls, both the cis and trans forms of the nonimmobilizer 1,2-dichlorohexafluorocyclobutane (F6), were docked to the same binding site. This compound is without known potency for response to a painful stimulus (hence the name, nonimmobilizer) and is experimentally devoid of activity at the GABAaR. Mihic et al. (1994) *Mol Pharmacol* 46:851-7. As additional controls, the following propofol analogs, noted for their inactivity at the GABAaR (Krasowski et al. (2001) *J Pharmacol Exp Ther* 297:338-51), were docked: dicyclohexylphenol, ditert-2,6-butylphenol, cyclopentylphenol and dicyclopentylphenol. Linear regression analysis correlating the best negative CDocker score of each compound with the negative logarithm of its experimentally derived GABAaR EC50 for potentiation was performed within Microsoft Excel 2007 (Microsoft Inc., Redmond, Wash.).

With docking validation derived from the aforementioned calculations, a new set of in silico molecular docking calculations was performed using the series of known etomidate-like derivatives described by Biggio et al. See Asproni et al. (2005) *J Med Chem* 48:2638-45. The most potent agent for GABAaR potentiation within this series is TG41. See FIG. 1A and Mascia et al. (2005) *Eur J Pharmacol* 516:204-11. However, since these compounds contain an unbonded imidazole nitrogen, which is likely to inhibit 11-beta hydroxylase corticosteroid biosynthesis (see below), and as has been known to occur with etomidate, the structure of the most potent version of this series was modified to a completely new compound. See FIG. 1B. For comparison, a carbo version of etomidate has recently been shown to display lower inhibition of adrenocortical steroid biosynthesis. See, Shanmugasundararaj et al. (2013) *Anesth Analg* 116:1249-56, and U.S. Pat. No. 8,765,973.

The Chemical Abstracts Database was searched for other structures with at least 80% similarity to carbo-1n for purposes of in silico docking and in vitro and in vivo testing. The structures of the selected compounds are displayed in Table 1:

TABLE 1

Structures of compounds identified by in silico modeling based on similarity to carbo 1n.

| Cpd. | Structure |
|---|---|
| A | 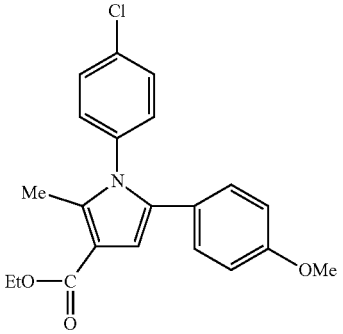 [SMILES: CCOC(=O)c1cc(-c2ccc(OC)cc2)n(-c2ccc(Cl)cc2)c1C] |
| B | 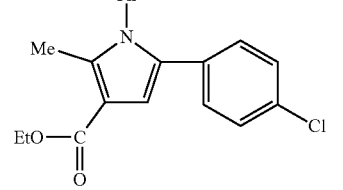 |

TABLE 1-continued
Structures of compounds identified by in silico modeling based on similarity to carbo 1n.
| Cpd. | Structure |
|---|---|
| C | 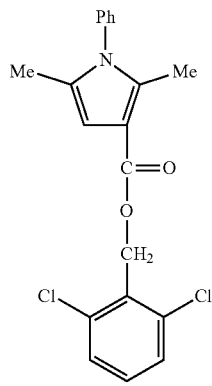 [SMILES: Cc1cc(C(=O)OCc2c(Cl)cccc2Cl)c(C)n1-c1ccccc1] |
| D | 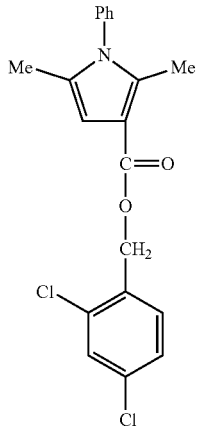 [SMILES: Cc1cc(C(=O)OCc2ccc(Cl)cc2Cl)c(C)n1-c1ccccc1] |
| E | 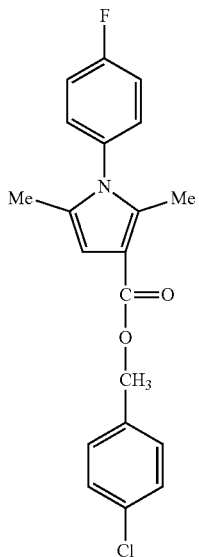 [SMILES: Cc1cc(C(=O)OCc2ccc(Cl)cc2)c(C)n1-c1ccc(F)cc1] |
| F | 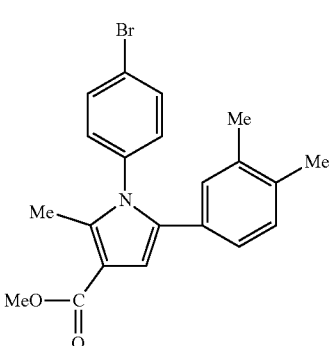 |
| G | 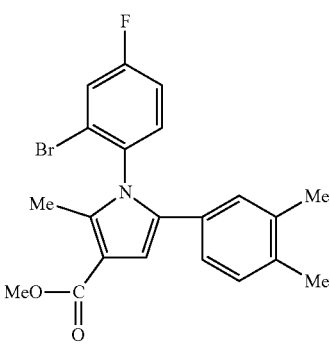 [SMILES: COC(=O)c1cc(-c2ccc(C)c(C)c2)n(-c2ccc(F)cc2Br)c1C] |
| H | 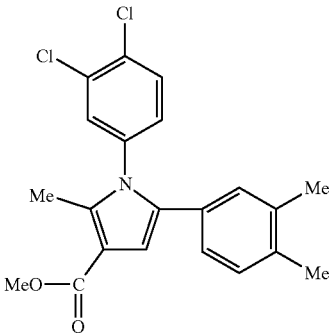 [SMILES: COC(=O)c1cc(-c2ccc(C)c(C)c2)n(-c2ccc(Cl)c(Cl)c2)c1C] |
| J | 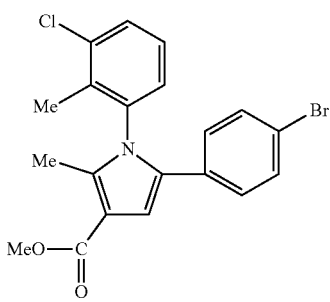 [SMILES: COC(=O)c1cc(-c2ccc(Br)cc2)n(-c2cccc(Cl)c2C)c1C] |

TABLE 1-continued

Structures of compounds identified by in silico modeling based on similarity to carbo 1n.

| Cpd. | Structure |
|---|---|
| K | 1-(4-bromophenyl)-2-(4-bromophenyl)-5-methyl-4-(methoxycarbonyl)pyrrole |
| L | 1-(2,4-difluorophenyl)-2-phenyl-5-methyl-4-(ethoxycarbonyl)pyrrole |
| M | 1-(2,3-dichlorophenyl)-2-phenyl-5-methyl-4-(ethoxycarbonyl)pyrrole |

The receptor binding site for this series was created by using the previously formed propofol docking site and allowing residues within a 5 angstrom radius of the docked propofol or the centroid of the three critical amino acids noted above to be flexible, while maintaining rigidity of the remainder of the protein. The binding site was created by allowing the most potent of the etomidate-like derivatives, compound 1n, to dock into its most favorable pose while relaxing the adjacent amino acid sidechains, thereby creating an induced-fit binding site which would be most favorable to ion channel opening given the great potency and relative rigidity of compound 1n. Docking was performed using the Flexible Docking algorithm within Discovery Studio 4.0 (Accelrys inc., San Diego, Calif.). Once obtained, further flexible docking was performed using the aforementioned etomidate-like derivatives within the series pertaining to compound 1n, the carbo-1n derivative itself, and finally 12 compounds with at least 80% similarity to carbo-1n. The settings for this calculation allowed for a 5 angstrom radius about the centroid of the binding pocket within which amino acid sidechains were allowed to move. This protocol allows for some receptor flexibility during docking of flexible ligands. Koska et al. (2008) *J Chem Inf Model* 48:1965-73. The side-chains of specified amino acids are allowed to move during docking. This allows the receptor to adapt to different ligands in an induced-fit model. The protocol uses a combination of components from other protocols to perform the docking, and is based on methods within CHARMm to sample side-chain and ligand conformations.

The Flexible Docking protocol performs the following steps:

1. Calculate receptor side-chain conformations: Initially, the protocol creates protein side-chain conformations using the ChiFlex algorithm.
2. Create ligand conformations: Low energy ligand conformations are created for the docking process using the Generate Conformations routine.
3. Perform initial placement of the ligand conformations: The ligand conformations are docked into the active site of each receptor side-chain conformation using LibDock.
4. Clustering to remove similar ligand poses: Poses are clustered regardless of the protein conformation since the protein conformations are rebuilt during the next step.
5. Refine side-chains: In the presence of the ligand, the specified receptor side-chain residues are refined using the ChiRotor algorithm.
6. Refine docking: A final simulated annealing and energy minimization of each ligand pose is performed using CDOCKER. CDocker energy scores as well as CDocker Interaction Energy scores were obtained for multiple poses of each ligand within the 1n favorable binding site.

The best score for each ligand was then correlated with GABAaR potentiation EC50 for those compounds in the 1n series where such data was available. Such scores were further obtained for carbo-1n and similar compounds to determine possible predicted potencies.

4. Molecular Modelling of the 11-Beta Hydroxylase Enzyme and its Interactions with Etomidate, Carboetomidate, 1n and carbo 1n Anesthetics interact with many functional proteins resulting in a variety of important side effects. In particular, etomidate has a strong inhibitory effect on a critical enzyme for steroid biosynthesis, 11-beta hydroxylase (11CYPB). For many patients this effect can result in catastrophic adrenocortical suppression. Any complete understanding of these effects is predicated on a more thorough description of such drug-protein interactions at a molecular level. While the exact molecular structure of all forms of 11CYPB remain unknown, significant progress has been made towards understanding their interactions with anesthetics using molecular modeling as noted here. A molecular model of 11CYP was therefore built, and in silico docking analyses of several important ligands to its binding site were performed. All protein construction calculations were performed in the Discovery Studio 3.5 software suite (Accelrys, San Diego, Calif.). The amino acid sequence of the human 11CYPB was obtained from the National Center for Biotechnology database. A BLAST sequence search was performed using this sequence to search for sequences of high homology from those with known three dimensional structures. The four best scored homologous human sequences were downloaded as 3D coordinates from the Research Collaboratory for Structural Biology (RCSB) database. A multiple structure alignment was performed via the SAlign algorithm to create a sequence profile based upon this structural alignment. Similarly, a BLAST sequence search was performed using the human 11CYPB sequence to search for sequences of high homology from all known amino acid sequences. A multiple sequence alignment was performed from the resulting 211 sequences identified with good homology using the ClustalW algorithm. A profile (from the multiple structure alignment) to profile (from the multiple sequence alignment) alignment was then performed with ClustalW so as to align the sequence of the unknown structure with those of the known structures. The Modeler module was used for assignment of coordinates for aligned amino acids, the construction of possible loops, and the initial refinement of amino acid sidechains. Normal mode analysis was performed using the LAABEN elastic network algorithm. Partial atomic charges for the heme moiety were computed using a combined quantum mechanics-molecular mechanics single point calculation for the heme group region using DMol density functional theory and a PBE functional, while the remainder of the complex was treated with a CHARMm molecular mechanics forcefield. Molecular docking of etomidate and carboetomidate stereoisomers, as well as the 1n and carbo 1n compounds, was performed with the CDocker algorithm as noted above.

5. Behavioral Studies of Newly Identified Lead Compounds in North American Tadpoles Anesthesia is defined as the combination of a lack of movement to a given stimulus, lack of awareness, amnesia and analgesia. The surrogate of such is manifest in the tadpole as the loss of righting reflex (LORR). Early prelimb-bud stage American bullfrog Rana catesbeiana tadpoles (5 per 50 ml beaker) were placed in room temperature oxygenated water buffered with 2.5 mM Tris HCl buffer (pH=7.4) and containing a concentration of test compound ranging from 0.11 uM-1 mM. Tadpoles were manually tipped every 5 min with a glass rod or stream of water until their righting reflex response stabilized or 120 minutes elapses. Tadpoles were deemed to have attained LORR if they failed to right themselves within 5 seconds after being turned over on their back. At the end of each study, tadpoles were transferred to fresh water to assess whether the anesthetic action was reversible.

6. Electrophysiology in Hippocampal Brain Slices

The activity of Compound B was assessed on native GABA-A receptors using well-established electrophysiological techniques in the CA1 region of the hippocampus obtained from acutely dissected rodent brains and as discussed in previous work. MacIver (2014) Anesth Analg 119:558-69.

a. Brain Slice Preparation:

Experimental protocols were approved by the animal use committee at Stanford University and adhered to published guidelines of the National Institutes of Health and the Society for Neuroscience. Brain slices were prepared from male Sprague-Dawley rats that had been deeply anesthetized with isoflurane. The brain was quickly removed and placed in ice-cold artificial cerebrospinal fluid (ACSF) that was saturated with 95% $O_2$ and 5% $CO_2$ (carbogen) to achieve a pH of 7.4. The ACSF was composed of the following ions dissolved in spectrophotometry grade water (EMD Chemicals Inc., Billerica, Mass.) and stated in millimolar concentrations: Na 151.25, Cl 131.5, $HCO_3$ 26, K 2.5, Ca 2, Mg 2, $SO_4$ 2, $H_2PO_4$ 1.25, and glucose 10. Coronal brain slices were prepared using a vibratome (Model 1500, Technical Products International Inc., St. Louis, Mo.) and 400-µm-thick slices were hemisected and placed on cellulose filter papers. They were stored at a gas (carbogen)-liquid (ACSF) interface in a holding chamber for at least 1 hour before use.

Single slices were transferred to a recording chamber and submerged in room temperature (22° C.) ACSF flowing at a rate of 3.0 mL/min. ACSF was saturated with carbogen by bubbling the solution for at least 15 minutes before use. Teflon storage vessels and tubing were used throughout the perfusion system to ensure minimal loss of anesthetic agents due to diffusion or binding.

b. Electrophysiology:

Evoked field potentials were measured using thin-walled glass pipettes (1.0 ID, 1.5 OD; Garner Glass Co., Claremont, Calif.) filled with ACSF. Electrodes were placed in stratum radiatum to record field excitatory postsynaptic potentials (EPSPs) or placed in stratum oriens, close to the CA1 cell body layer, to record population spikes. Bipolar tungsten microelectrodes (10 Mohm; Frederick Haer & Co., Bowdoin, Me.) were placed in stratum radiatum and used to stimulate Schaffer-collateral fibers to synaptically drive CA1 neurons. Single- or paired-stimulus pulses (0.01-0.03 milliseconds duration; unipolar, 10-80 µA at 1.0-8.0 V) were generated from constant current stimulus isolation units (6D; Grass Instruments, Warwick, R.I.) driven by a Grass S8800 stimulator. Paired-pulse stimulation was used to measure anesthetic effects on tonic and fast (first pulse) and slow (second pulse) inhibitory pathways in the CA1 area neural circuit.

Recorded signals were conditioned using an Axoclamp 2B preamplifier (Axon Instruments, Sunnyvale, Calif.) with a bandpass from DC to 30 kHz and gain of ×10. Signals were further amplified (×100) and conditioned (DC offset, DC to 30 kHz) using a differential instrumentation amplifier in single-ended mode (Model 440; BrownLee Precision, Santa Clara, Calif.). Signals were digitized at 10 kHz using a National Instruments analog to digital converter (USB 6009) and Igor Pro software (Wavemetrics Inc., Santa Clara, Calif.) on a MacBook Pro computer. Responses were measured and plotted in real time to ensure that stable baselines (<±2.0% variation) were recorded for at least 20 minutes before the experiments began. Preparations showing any upward or downward drift in baseline were not used for experiments.

Drug Solutions:

Compounds were applied in the ACSF perfusate after at least 15 minutes of equilibration, by bubbling into the ACSF with a carbogen carrier gas. The compounds were solubilized using 0.5% dimethyl sulfoxide and vortexed into stock solutions before being serially diluted into prebubbled (carbogen) ACSF solutions to achieve final concentrations, just before testing. The compounds were added as at least a ¹⁄₁₀₀₀ final dilution from concentrated stock solutions in water. A single concentration of the compound was tested on each slice preparation to avoid tachyphylaxis or cross-contamination of drug effects. The entire perfusion system was cleaned and replaced on a regular basis to avoid cross-contamination between anesthetics and tested compounds.

c. Data Analysis:

Time-matched experiments were averaged together using IgorPro software and graphed as mean±SD of measured responses versus experimental time (in minutes; sampled 3 times per minute). Averaged experimental data are displayed as a percentage of control responses normalized to the size of baseline responses for 20 minutes preceding the start of each experiment.

Statistical analyses (analysis of variance [ANOVA] with post Tukey test) comparing non-normalized control, unknown compound responses and washout were performed using Igor Pro software. In all cases, "n" refers to individual experiments conducted on separate slices, usually from different rats.

Results
1. In Silico Model Construction

The sets of structural alignments from both the SAlign and 3DMA algorithms revealed that there was clear consensus as to the spatial location of residues relevant to anesthetic effects based on all templates, except for the intermediate resolution structure of nAChR (2BG9). That is, when multiple sequence alignments are performed between all of the structures noted previously along with the GABAaR and the GlyRa1, the multiple structure alignment agrees with the positions of homologous residues except for the structure of 2BG9. These issues with the 2BG9 structure have been noted by others as well. Hibbs et al. (2011) *Nature* 474:54-60; Chiara et al. (2003) *Biochemistry* 42:13457-67; Ernst et al. (2005) *Mol Pharmacol* 68:1291-1300. For the anesthetic effect in the human GlyRa1, these positions are those that are homologous to residues ILE 229, SER 267 and ALA 288. The 2BG9 coordinates had gross discrepancies of amino acid positions of homologous residues known to alter anesthetic modulation in several transmembrane domains. The specific misaligned residues were dependent on the structural alignment algorithm, but in neither case could the location of all relevant residues be completely satisfied by the 2BG9 structure. In particular, using the SAlign algorithm, in the alpha 1 subunit of the nAChR, it was LEU 257 on TM2, and LEU 279 on TM3 that did not align with their homologous positions on the remaining templates, despite multiple sequence alignment to the contrary. Optimizing to a slightly different structural alignment with the 2BG9 template using the 3DMA algorithm, it was ILE 220 on TM1 and LEU 257 on TM2 that could not align with their homologous positions on the remaining templates. This result was the justification for not using 2BG9 as a template for subsequent modeling, in addition to the further rationale for using GluCl noted in the Discussion section.

Once the GABAaR models were constructed, the preponderance of secondary structure in the extracellular native ligand binding domain remained in the beta sheet conformation, while that of the transmembrane domain remained as tetrameric alpha helical bundles. This was noted as a consensus in the models derived using the Modeler method. The models proved extraordinarily similar across the entire pentameric assembly as well as in the important putative transmembrane anesthetic binding clefts. As noted in the inventors' previous work for the GlyRa1, the majority of residues in homologous proteins that were experimentally labeled as facing hydrophilic regions also lined the water accessible portions of the model structures, while those which were experimentally labeled by lipophilic reagents were often accessible to the lipid membrane portion of the model. Bertaccini et al. (2010) *J Chem Inf Model* 50:2248-55. Likewise, experimental data on cysteine crosslinking of adjacent residues may be partially accounted for with these models as they are consistent with the ability to form disulfide bonds between specific intersubunit residue positions on the alpha TM1 subunit and the adjacent beta TM3 subunit. Bali et al. (2012) *J Biol Chem* 287:27762-70; Bali et al. (2009) *J Neurosci.* 29:3083-92.

Figure 2:
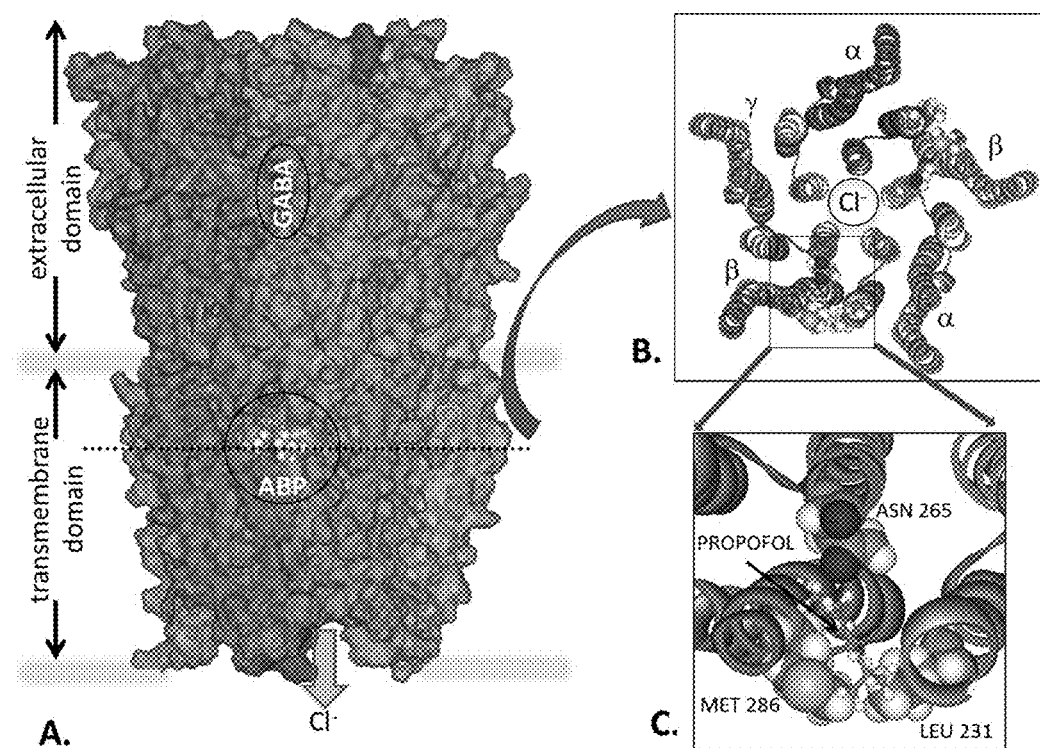
FIG. 2. (A) Illustrates a 3-dimensional model of the GABA receptor, including the transmembrane domain, the extracellular domain, and the GABA binding site. (B) Shows a cross-section of the receptor model in the region of the proposed anesthetic binding site. (C) Shows a detailed structural model around the residues believed to be involved in modulating anesthetic action, as well as a bound molecule of propofol at this site.

The three residues in the mouse GABAaR which were in homologous positions and notable for modulating anesthetic action within the transmembrane domain (beta 3 N265, MET286 and alpha L231), continue to line the intersubunit interface between alpha and beta subunits after energy optimization (see FIG. 2), as noted in previous models. Bertaccini et al. (2010) *J Chem Inf Model* 50:2248-55.

2. High Throughput Molecular Docking Analyses

Figure 3:
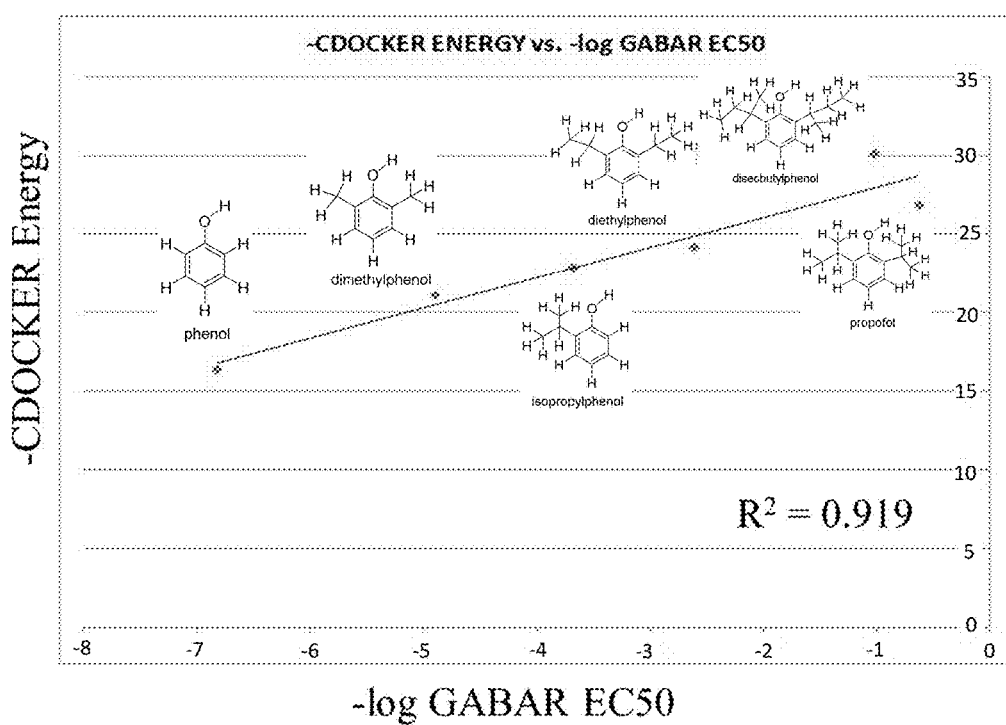
FIG. 3. Results of the docking of propofol analogues, using the CDocker Interaction Energy score (CDIE).

Docking of the propofol derivative series to the region bound by these residues showed strong linear correlation with experimentally derived GABAaR potentiation EC50 (see FIG. 3) as suggested by an $R^2$ of 0.92.

CDocker scoring was also validated by the results of the control compounds with known inactivity at the GABAaR. The CDocker scores for dicyclohexylphenol, ditert-2,6-butylphenol and cyclopentylphenol were −14.3 kcal/mol, −13.2 kcal/mol, and −6.0 kcal/mol, respectively. These latter three are all significantly worse than the lowest potency agonist studied (phenol with a CDocker score of −16.5 kcal/mol and an EC50 of 920 uM), suggesting the latter three predicted potencies are well into the millimolar range and beyond the ranges experimentally tested by Kraswoski et al. Krasow ski et al. (2002) *J Med Chem* 45:3210-21. The CDocker binding score was very unfavorable for dicyclopentylphenol (6.5 kcal/mol). The so-called "F6" nonimmobilizer from the Eger group was docked in both its cis and trans conformations. The CDocker binding energies were grossly unfavorable for both versions of this compound (cis=29.1 kcal/mol and trans=28.4) to the putative anesthetic binding site. This is in stark contrast to the CDocker energy scores for all of the propofol derivatives studied here that are agonists and which are clearly in the energetically favorable negative range. Bertaccini et al. (2013) *Anesthesiology* 119:1087-95.

Figure 4:
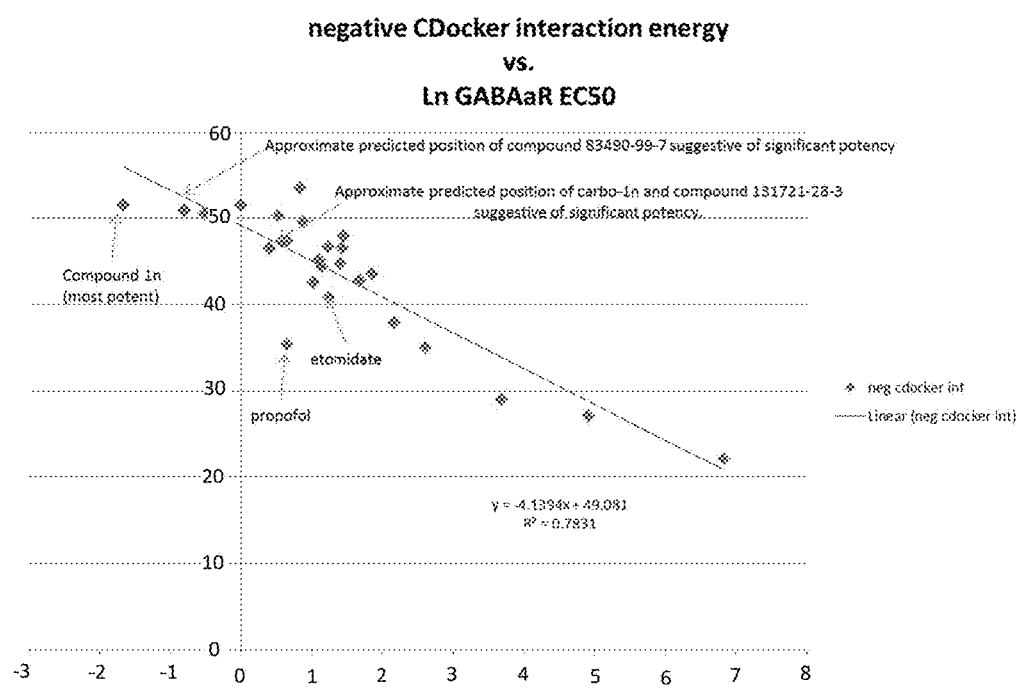
FIG. 4. Plot of negative CDocker interaction energy as a function of the logarithm of GABAaR $EC_{50}$.

Further docking of the new lead compound series showed strong correlation of a slightly different docking score, the CDocker Interaction Energy score (CDIE), with experimentally derived GABAaR potentiation EC50 (see FIG. 4). This correlation not only spanned the previously studied propofol-like compounds, but included several of the etomidate-like derivatives of Biggio et al. as well as the carbo-1n compound (FIG. 1(B)) in addition to the 12 compounds identified for comparison with carbo-1n (Table 1). In particular, compound A is roughly an order of magnitude less potent than compound 1n which has a known EC50 for GABAaR potentiation of 0.19 uM. Compound B has a predicted potency close to that of propofol which is further born out by the electrophysiology data below. As is demonstrated below, the EC50 for GABAaR potentiation of compound A is approximately 1.5 uM in tadpoles (Table 2).

Figure 5:
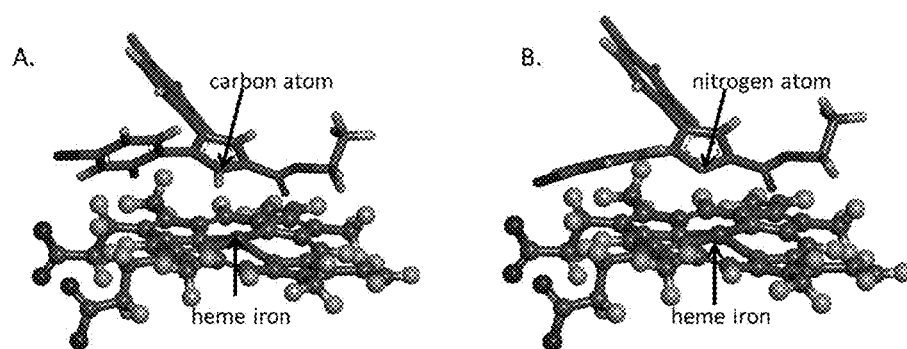
FIG. 5. (A) Model of the most likely orientation of carbo-1n in relation to the heme iron of the FAD moiety within the binding site of 11-beta hydroxylase. (B) Model of the most likely orientation of compound 1n in relation to the same heme iron. Note the proximity of the imidazole nitrogen in compound 1n to the heme iron, which allows the covalent binding between the two and the lack of such binding in carbo-1n.

3. Molecular Modelling of the 11 Beta Hydroxylase Enzyme and its Interactions with Etomidate, Carboetomidate, 1n and carbo-1n The BLAST derived scores and CLUSTALW profile to profile alignment demonstrates reasonable sequence similarity between 11CYPB and the modeling templates. The model of the 11CYPB has a cavity of approximately 810 cubic angstroms in volume and can readily accommodate a steroid analog. Within the lowest frequency, highest amplitude natural harmonic motions of this channel, normal mode analyses suggest that this cavity is located in a region of reasonable flexibility which could be critical to a "clamshell-like" opening motion for binding site access. While etomidate, carboetomidate, 1n and carbo-1n have docking poses which show a potentially reversible carbonyl interaction with the heme Fe, only etomidate and compound 1n clearly show an imidazole nitrogen in a position for the undesirable irreversible covalent interaction with the heme Fe (see FIGS. 5A and 5B). Therefore, it is predicted that carbo-1n, and the compounds of Table 1, should not be associated with significant irreversible inhibition of steroid biosynthesis. Homology modeling produces a model of the 11CYP that reveals a binding site that helps to explain the differential binding to, and inhibition of, 11CYP for ring structures containing an imidazole nitrogen and, despite similar ligand pose within the binding site, the inability for such irreversible interactions when a single imidazole nitrogen is changed to a carbon atom.

4. Behavioral Studies of Newly Identified Lead Compounds in North American Tadpoles The compounds identified by, and analyzed in, the computer modeling described above (see Table 1) have been demonstrated to act as anesthetics in an animal model system. The effects of these compounds in loss of righting reflex (LORR) assays in tadpoles are provided in Table 2:

TABLE 2

Effects of compounds on LORR in tadpoles.

| Cpd. | $EC_{50}$ (uM) for LORR |
|---|---|
| A | 1.5 |
| B | 0.53 |
| C | ~5 |
| D | ~20 |
| E | ~40 |
| F | ~20 |
| G | ~3 |
| H | >40 |
| J | >40 |
| K | ~40 |
| M | ~20 |

Figure 6:
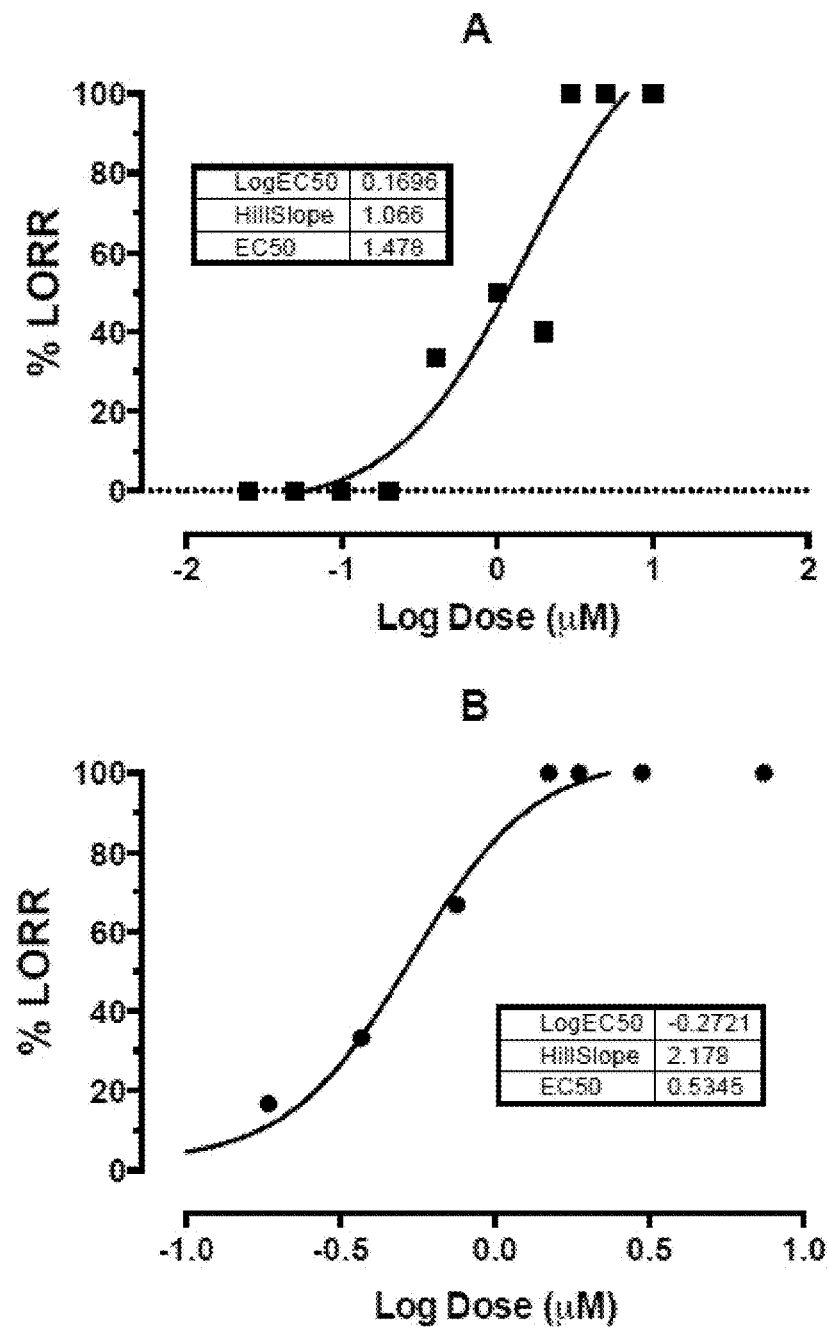
FIG. 6. Dose-response curves for the effects of compounds A (panel A) and B (panel B) in the tadpole Loss of Righting Reflex assays. The units of the x-axis are log(μM).

Dose-response curves for two of the more potent compounds are shown in FIG. 6. Panel A=Compound A; Panel B=Compound B. The effectiveness of each of the compounds as anesthetics is similar to that of propofol in these assays.

5. Electrophysiology in Hippocampal Brain Slices

Figure 7:
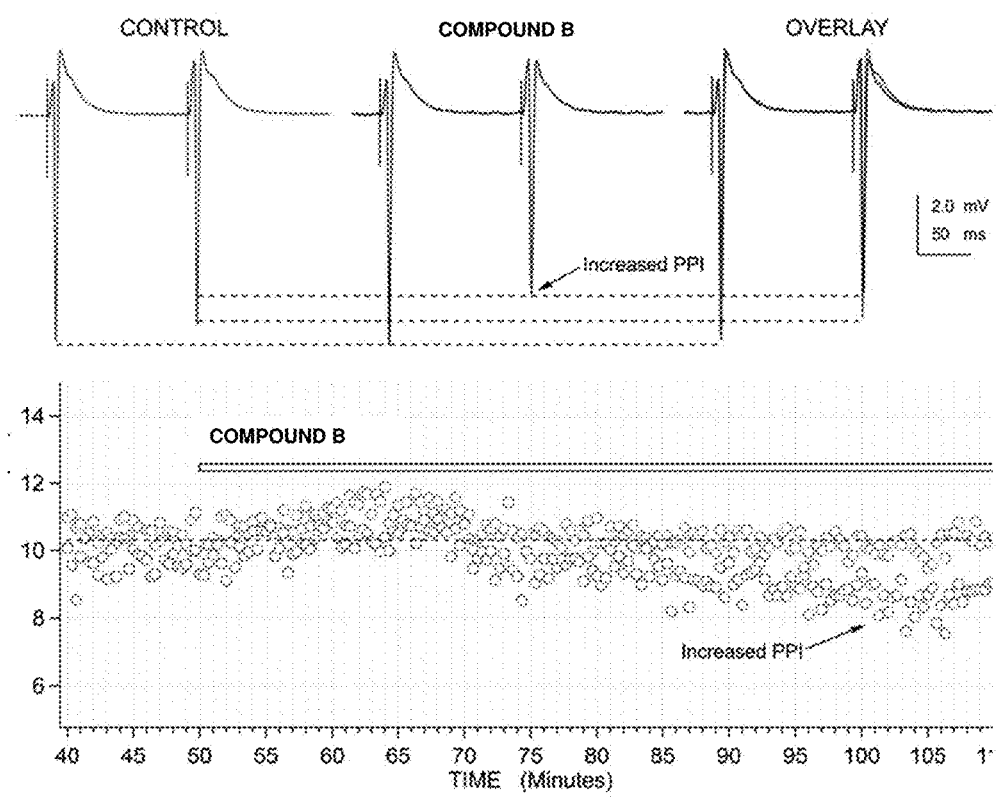
FIG. 7. Effect of compound B on a hippocampal brain slice preparation.

The effect of compound B on a hippocampal brain slice preparation analyzed as described above is shown in FIG. 7. Here the clear production of the phenomenon known as paired pulse inhibition can be seen. The occurrence of such is clear evidence of an effect mediated via the GABAa receptor. This initial effect was noted at a concentration of 100 uM of test compound compared to a similar response for propofol in the 10 uM range. This discrepancy may be explained by differential kinetics and/or metabolism of the test compound in the hippocampal preparation compared to that of propofol itself.

Discussion:

For many years, homology modeling of the GABAaR has been hampered by a limited amount of highly homologous structural templates. In 1985, the first low resolution cryo-electron micrograph of the homologous nAChR was released. Brisson et al. (1985) Nature 315:474-7. Over the next 20 years, this model was refined to the intermediate resolution of 4 Å and published in the Research Collaboratory for Structural Biology protein databank as entry 2BG9. Unwin (2005) J Mol Biol 346:967-89. The model was a tremendous accomplishment at the time. However, while the 4 Å cryo-electron micrograph provided great insight into the overall secondary, tertiary and quaternary structure of this class of ligand-gated ion channels, the exact atomic delineation of individual amino acid assignments in three dimensional space was unclear. Specifically, this cryo-electron micrograph was the consensus of micrographs over the 4 different subunit subtypes within the Torpedo nAChR (2 alpha subunits, one beta, one gamma and one delta). At 4 Å resolution, the globular appearance of sidechain identities is insufficient to make precise identifications of individual amino acids.

Given the recently-released NMR structures of the transmembrane domains of the alpha 4 and beta 2 nAChR subunits, and their high homology to the torpedo nAChR, discrepancies in the amino acid assignments within the subunits of torpedo nAChR (2BG9) are apparent, making this a much less desirable modeling template from which to build a GABAaR structure. Cui et al. (2012) Biochim Biophys Acta 1818:617-26.

The GABAaR, GluCl, and GLIC templates were initially considered for homology modeling, based on their homology to the GABAaR sequence, the availability of a whole pentameric ion channel construct, and their low root mean square deviation from the NMR structures of the alpha and beta subunits of the nAChR. The use of only templates with all 5 subunits, as is the case in all three, arranged with a pentameric symmetry is considered important for the analysis of anesthetic interactions, since the location of this anesthetic binding site within the GABAaR is actually between specific alpha and beta subunits within the transmembrane domain. Furthermore, the GluCl structure is thought to be in the open state of the ion channel pore, a feature believed to be important for anesthetic binding, since the anesthetic potentiation of the GABAaR is believed to come from the binding to and stabilization of the open channel state. Forman et al. (2011) Can J Anaesth 58:191-205. For comparison, the published structure of GLIC is thought to be either in the closed or partially open state, and the published structure of GABAaR beta 3 is thought to be in the desensitized state. It is also the GluCl structure noted in the 3RIF and 3RHW templates that actually shows a ligand, ivermectin, bound in the same transmembrane location as an anesthetic binding site in the homologous GABAaR. Ivermectin is known to produce a similar potentiation for the GluCl as anesthetics do for the GABAaR. This GluCl structure also has the native bound ligand, glutamate, which further tends the construct towards an open structure. Additionally, this structure would be similar to the condition of anesthetic potentiation of the GABAaR in which its native ligand, gamma amino butyric acid (GABA), must be present. Furthermore, GluCl is derived from the eukaryote, C. elegans, as opposed to GLIC, which is derived from the prokaryote, G. violaceus. Since eukaryotes have cholesterol in their membrane structure and prokaryotes do not, GluCl may be more representative of the proper intersubunit helical packing found in higher eukaryotic organisms. For at least these reasons, the GluCl template formed the basis for modeling in this disclosure.

When residues that are known to modulate anesthetic activity from homologous positions in different LGICs are mapped to the sequences of known template structures, consensus structural alignment based on the remaining 5 templates excluding 2BG9 revealed the consistent formation of an intersubunit anesthetic binding cavity within the transmembrane domain of these ligand-gated ion channels (see FIG. 2C). This consensus lends greater confidence to the overall model building process and to further pursuit of validation analyses. Such analyses have included the ability to simulate the large-scale motion of the channel that was performed in previous efforts by the inventors in which an "iris-like" motion of channel gating was described. Bertaccini et al. (2010) ACS Chem. Neurosci. 1:552-558; Bertaccini et al. (2008) J Chem Inf Model 48:855-60; Bertaccini et al. (2005) 7th International Conference on Basic and Systematic Mechanisms of Anesthesia. Nara, Japan, Elsevier, pp 160-163. Further validation of the process also came in the form of channel responses to ligand binding via long term molecular dynamics simulations. This has been accomplished with molecular dynamics simulations in previous models of the GlyRa1 in the presence and absence of ethanol for 1 microsecond periods. Murail et al. (2011) *Biophys J* 100:1642-50. However, actual channel gating occurs on timescales that are orders of magnitude larger and will require computational resources not currently available. Additional validation is now presented in the instant disclosure via the correlation of relative binding energy scores with experimentally derived measures of GABAaR potentiation.

The location of anesthetic binding sites within the LGICs continues to be a topic of debate but is not critical for the practice of the instant invention. One of the proposed sites has been examined in this disclosure. There is evidence that anesthetics bind to sites within the transmembrane subunits of homologous proteins, specifically in GLIC and the *Erwinia chrysanthemi* ion channel (ELIC). In former models of various LGICs based on older templates, certain constructs were presented which postulated such an intrasubunit binding site for anesthetics within the glycine receptor as well. Bertaccini et al. (2005) *J Chem Inf Model* 45:128-35. However, newer more homologous templates allow the construction of more robust models in which there is a convergence of residues relevant to anesthetic modulation on a common intersubunit binding site. As suggested in a recent publication from the inventors' laboratory (Murail et al. (2012) *PLoS Comput Biol* 8:e1002710), a key site for anesthetic and alcohol action may be between the transmembrane subunits. An even more interesting occurrence has been shown in the crystal structure of *Erwinia chrysanthemi* ion channel (ELIC) with the anesthetic bromoform, in which both potentiation and inhibition have been noted by binding of the anesthetic to an intersubunit transmembrane cleft (Spurny et al. (2013) *J Biol Chem* 288:8355-64) in addition to effects within the pore and extracellular domains. Furthermore, the extracellular domain within this class of ion channels involves its own set of inter- and intrasubunit clefts. Pan et al. have demonstrated that the intravenous general anesthetic, ketamine, binds at an intersubunit site and causes inhibition of the channel in the extracellular or native ligand binding domain of the protein. Pan et al. (2012) *Structure* 20:1463-9. However, the instant work is to merely examine one of these putative binding sites which has been extensively studied in the inventors' previous modeling studies and in the experimental work of other groups. This binding site has clearly been shown to be both necessary and sufficient to mediate anesthetic effects in several circumstances. Bertaccini et al. (2010) *J Chem Inf Model* 50:2248-55; Murail et al. (2012) *PLoS Comput Biol* 8:e1002710; Jenkins et al. (2001) *J Neurosci* 21:RC136; Mihic et al. (1997) *Nature* 389:385-9.

Once a binding site has been identified in the computer model, further validation and utility of the model must come from predictions of anesthetic affinity and possible activity in compounds that have heretofore not been known to have anesthetic potency. This goal would be accomplished through the application of a wide variety of molecular docking and scoring schemes which allow individual compounds to be docked to a designated anesthetic binding site within the protein in question, as has been described recently. Liu et al. (2012) *Anesth Analg* 114:947-55. Any such endeavor is dependent on the ability to at least predict the orders of potency within a series of similar anesthetic ligands from a qualitative standpoint and, when feasible, predict a quantitative measure as well. The energetic parameter which should ultimately correlate with such potency is the free energy of ligand binding. However, total free energy is dependent on both enthalpy and entropy. Accounting for the binding entropy changes can be very difficult using computational methods. Ligands which vary markedly in size and shape could have very different entropic contributions to binding that are poorly accounted for by anything other than very complex and computationally expensive free energy perturbation calculations that are impractical for high throughput screens. However, within a reasonably similar congeneric series of ligands, as utilized here, such an entropic contribution can be assumed to be similar amongst members, with the enthalpic contribution of binding dominating the relative interactions. It is this enthalpic contribution that is most closely related to the docking scores presented here. With this, the instant model of an anesthetic binding pocket has characteristics that allow reasonable correlation of ligand enthalpic docking scores with actual experimentally derived measures of GABAaR potentiation for the set of propofol and etomidate-like derivatives studied.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A method of treatment, comprising administering to a subject in need thereof a concentration of a compound sufficient to induce or maintain anesthesia in the subject, wherein the compound is represented by structural formula (I):

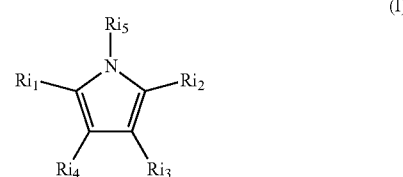

or a pharmaceutically acceptable salt thereof, wherein:
$R_{i1}$ and $R_{i2}$ are independently H, a lower alkyl group, or a phenyl group, wherein the alkyl group and phenyl group are optionally and independently substituted with one or more alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido groups, and wherein two adjacent substituent groups can combine to form a ring;

either $R_{i3}$ or $R_{i4}$ is —C(O)OR$_e$, and the other group is H or a lower alkyl group;

$R_e$ is alkyl, alkenyl, alkynyl, aryl, aralkyl, heteroaryl, heteroaralkyl, cycloalkyl, cycloalkenyl, heterocyclyl, or heterocyclylalky, and is optionally substituted with alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido; and $R_{i5}$ is a phenyl group optionally substituted with one or more alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido groups, and wherein two adjacent substituent groups can combine to form a ring.

2. The method of claim 1, wherein in the compound of structural formula (I), either of $R_{i1}$ and $R_{i2}$ is an optionally substituted phenyl group, and the other is H or an unsubstituted lower alkyl group.

3. The method of claim 2, wherein in the compound of structural formula (I), the $R_{i1}$ or $R_{i2}$ optionally substituted phenyl group is optionally substituted with one or more alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido groups.

4. The method of claim 1, wherein in the compound of structural formula (I), $R_{i1}$ and $R_{i2}$ is each independently an unsubstituted lower alkyl group.

5. The method of claim 1, wherein in the compound of structural formula (I), $R_e$ is an optionally substituted lower alkyl or aralkyl group.

6. The method of claim 1, wherein in the compound of structural formula (I), $R_{i5}$ is a phenyl group optionally substituted with one or more alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido groups.

7. The method of claim 1, wherein in the compound of structural formula (I), either of $R_{i1}$ and $R_{i2}$ is a phenyl group optionally substituted with one or more alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido groups, and the other is H or an unsubstituted lower alkyl group;

$R_e$ is an optionally substituted lower alkyl or aralkyl group; and $R_{i5}$ is a phenyl group optionally substituted with one or more alkyl, alkoxy, hydroxyl, thio, amino, carboxy, carbonate, carbamate, guanidinyl, urea, halo, trihalomethyl, cyano, nitro, phosphoryl, sulfonyl, sulfonamido, or azido groups.

8. The method of claim 1, wherein the compound is represented by structural formula (II):

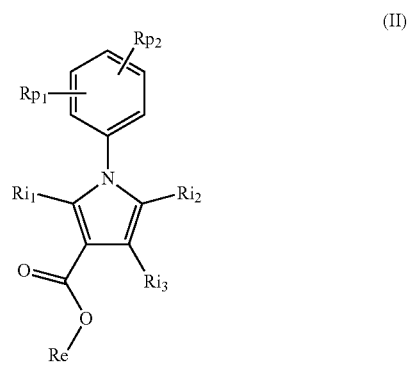

(II)

or a pharmaceutically acceptable salt thereof, wherein:

$R_{p1}$ and $R_{p2}$ are independently H, alkyl, alkenyl, alkynyl, alkoxy, alkanoyl, alkylamino, alkylthio, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido;

$R_{i1}$ and $R_{i2}$ are independently H, a lower alkyl group, or a phenyl group, wherein the alkyl group and phenyl group are optionally and independently substituted with one or more alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido groups, and wherein two adjacent substituent groups can combine to form a ring;

$R_{i3}$ is H or a lower alkyl group; and $R_e$ is alkyl, alkenyl, alkynyl, aryl, aralkyl, heteroaryl, heteroaralkyl, cycloalkyl, cycloalkenyl, heterocyclyl, or heterocyclylalky, and is optionally substituted with alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido.

9. The method of claim 8, wherein in the compound of structural formula (II), $R_{p1}$ and $R_{p2}$ are independently H, alkyl, alkoxy, or halo.

10. The method of claim 9, wherein in the compound of structural formula (II), either of $R_{i1}$ and $R_{i2}$ is an optionally substituted phenyl group, and the other is H or an unsubstituted lower alkyl group.

11. The method of claim 8, wherein in the compound of structural formula (II), $R_{i1}$ and $R_{i2}$ is each independently an unsubstituted lower alkyl group.

12. The method of claim 8, wherein in the compound of structural formula (II), $R_e$ is an optionally substituted lower alkyl or aralkyl group.

13. The method of claim 1, wherein the compound is represented by structural formula (III):

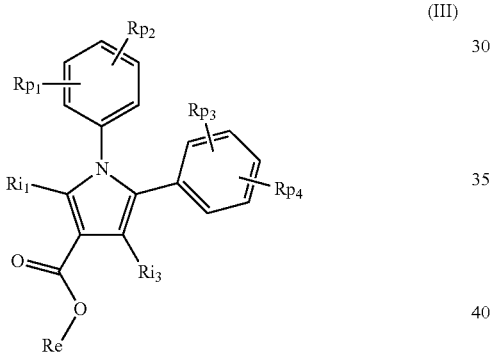

(III)

or a pharmaceutically acceptable salt thereof, wherein:

$R_{p1}$, $R_{p2}$, $R_{p3}$, and $R_{p4}$ are independently H, alkyl, alkenyl, alkynyl, alkoxy, alkanoyl, alkylamino, alkylthio, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido;

$R_{i1}$ is H, a lower alkyl group, or a phenyl group, wherein the alkyl group and phenyl group are optionally and independently substituted with one or more alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido groups, and wherein two adjacent substituent groups can combine to form a ring;

$R_{i3}$ is H or a lower alkyl group; and $R_e$ is alkyl, alkenyl, alkynyl, aryl, aralkyl, heteroaryl, heteroaralkyl, cycloalkyl, cycloalkenyl, heterocyclyl, or heterocyclylalky, and is optionally substituted with alkyl, alkenyl, alkynyl, alkoxy, alkanoyl, alkylamino, alkylthio, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkoxy, cycloalkanoyl, cycloalkamino, heterocyclyl, heterocyclyloxy, heterocyclylamino, heterocyclylalky, heterocyclylalkoxy, heterocyclylalkanoyl, heterocyclylalkamino, hydroxyl, thio, amino, amido, alkanoylamino, aroylamino, aralkanoylamino, alkylcarboxy, alkylcarbonyl, aminocarbonyl, alkylaminocarbonyl, carboxy, carbonate, carbamate, guanidinyl, urea, halo, trihalomethyl, cyano, nitro, phosphoryl, sulfonyl, sulfonamido, or azido.

14. The method of claim 13, wherein in the compound of structural formula (III), $R_{p1}$, $R_{p2}$, $R_{p3}$, and $R_{p4}$ are independently H, alkyl, alkoxy, or halo.

15. The method of claim 13, wherein in the compound of structural formula (III), Rd is H or lower alkyl.

16. The method of claim 13, wherein in the compound of structural formula (III), $R_e$ is an optionally substituted lower alkyl or aralkyl group.

17. The method of claim 1, wherein the anesthesia comprises tranquilization, sedation, amnesia, hypnosis, or insensitivity to noxious stimulation.

18. The method of claim 1, wherein the anesthesia is induced.

19. The method of claim 1, wherein the anesthesia is maintained.

20. The method of claim 1 comprising multiple administering steps or continuous administration.

* * * * *